US010626399B2

(12) United States Patent
Wyss-Coray et al.

(10) Patent No.: US 10,626,399 B2
(45) Date of Patent: Apr. 21, 2020

(54) METHODS OF TREATING COGNITIVE SYMPTOMS OF AN AGING-ASSOCIATED IMPAIRMENT BY MODULATING C-C CHEMOKINE RECEPTOR TYPE 3 (CCR3)

(71) Applicants: THE BOARD OF TRUSTEES OF THE LELAND STANFORD JUNIOR UNIVERSITY, Stanford, CA (US); THE UNITED STATES GOVERNMENT AS REPRESENTED BY THE DEPARTMENT OF VETERANS AFFAIRS, Washington, DC (US)

(72) Inventors: Anton Wyss-Coray, Palo Alto, CA (US); Thomas A. Rando, Stanford, CA (US); Markus Britschgi, Allscwil (CH); Kaspar Rufibach, Basel (CH); Saul A. Villeda, Lancaster, CA (US)

(73) Assignees: THE BOARD OF TRUSTEES OF THE LELAND STANFORD JUNIOR UNIVERSITY, Stanford, CA (US); THE UNITED STATES GOVERNMENT AS REPRESENTED BY THE DEPARTMENT OF VETERANS AFFAIRS, Washington, DC (US)

(*) Notice: Subject to any disclaimer, the term of this patent is extended or adjusted under 35 U.S.C. 154(b) by 0 days.

(21) Appl. No.: 16/067,771

(22) PCT Filed: Jan. 6, 2017

(86) PCT No.: PCT/US2017/012521
§ 371 (c)(1),
(2) Date: Jul. 2, 2018

(87) PCT Pub. No.: WO2017/120461
PCT Pub. Date: Jul. 13, 2017

(65) Prior Publication Data
US 2019/0024091 A1  Jan. 24, 2019
US 2019/0185862 A9  Jun. 20, 2019

Related U.S. Application Data

(63) Continuation of application No. 14/991,813, filed on Jan. 8, 2016, which is a continuation-in-part of
(Continued)

(51) Int. Cl.
*A61K 38/19* (2006.01)
*A61K 38/45* (2006.01)
*A61K 39/00* (2006.01)
*C12N 15/113* (2010.01)
*C07K 16/24* (2006.01)
*C07K 16/28* (2006.01)
*A61K 31/00* (2006.01)

*A61K 31/7088* (2006.01)
*C12Q 1/6883* (2018.01)

(52) U.S. Cl.
CPC .......... *C12N 15/1138* (2013.01); *A61K 31/00* (2013.01); *A61K 31/7088* (2013.01); *A61K 38/19* (2013.01); *A61K 38/45* (2013.01); *C07K 16/24* (2013.01); *C07K 16/28* (2013.01); *C12Q 1/6883* (2013.01); *A61K 2039/505* (2013.01); *C07K 2317/76* (2013.01); *C12N 2310/14* (2013.01); *C12N 2799/022* (2013.01); *C12N 2799/06* (2013.01); *C12Q 2600/136* (2013.01); *C12Q 2600/158* (2013.01); *C12Y 207/10001* (2013.01)

(58) Field of Classification Search
CPC .......... C12N 15/1138; C12N 2799/022; C12N 2799/06; C12N 2310/14; A61K 31/7088; A61K 38/19; A61K 38/45; A61K 31/00; A61K 2039/505; C12Q 1/6883; C12Q 2600/136; C12Q 2600/158; C07K 16/24; C07K 16/28; C07K 2317/76; C12Y 207/10001
See application file for complete search history.

(56) References Cited

U.S. PATENT DOCUMENTS 4,872,983 A   10/1989  Diamantoglou et al.
5,240,614 A    8/1993  Ofsthun et al.
(Continued)

FOREIGN PATENT DOCUMENTS

EP   0184040 B1   4/1993
EP   2341138 A1   7/2011
(Continued)

OTHER PUBLICATIONS

Takeda A, et al. (Jul. 9, 2009) Nature. 460(7252):225-230. (doi:10.1038/nature08151).*
Wang H, et al. (2011) Invest. Ophthalmol. Vis Sci. 52:8271-8277. (doi:10.1167/iovs.11-8230).*
Shen H-H, et al. (Dec. 2006) Acta Pharmacologica Sinica. 27(12):1594-1599. (doi: 10.1111/j.1745-7254.2006.00446.x).*
Adair et al., "Measurement of gelatinase B (MMP-9) in the cerebrospinal fluid of patients with vascular dementia and Alzheimer disease." Stroke. Jun. 2004;35(6):e159-62.
Adkins et al. "Toward a human blood serum proteome: analysis by multidimensional separation coupled with mass spectrometry." Mol Cell Proteomics. Dec. 2002;1(12):947-55.
Anderson et al., "High resolution two-dimensional electrophoresis of human plasma proteins." Proc Natl Acad Sci U S A. Dec. 1977;74(12):5421-5.
(Continued)

*Primary Examiner* — Robert S Landsman
(74) *Attorney, Agent, or Firm* — Casimir Jones, S.C.

(57) ABSTRACT

Methods of treating an adult mammal for an aging-associated impairment are provided. Aspects of the methods include modulating CCR3, e.g., by modulating eotaxin-1/CCR3 interaction, in the mammal in a manner sufficient to treat the mammal for the aging-associated impairment. A variety of aging-associated impairments may be treated by practice of the methods, which impairments include cognitive impairments.

24 Claims, 28 Drawing Sheets

Related U.S. Application Data application No. 14/280,939, filed on May 19, 2014, which is a continuation of application No. 13/575,437, filed as application No. PCT/US2011/022916 on Jan. 28, 2011, now abandoned.

(60) Provisional application No. 61/298,998, filed on Jan. 28, 2010.

(56) References Cited

U.S. PATENT DOCUMENTS

| | | | |
|---|---|---|---|
| 5,916,202 | A | 6/1999 | Haswell |
| 6,416,487 | B1 | 7/2002 | Braverman et al. |
| 6,419,830 | B2 | 7/2002 | Strom et al. |
| 6,423,024 | B1 | 7/2002 | Strom et al. |
| 6,632,174 | B1 | 10/2003 | Breznitz |
| 6,855,121 | B1 | 2/2005 | Chan et al. |
| 6,946,546 | B2 | 9/2005 | Vaughan et al. |
| 7,196,162 | B2 | 3/2007 | Quirk et al. |
| 7,368,542 | B2 | 5/2008 | McIntyre |
| 7,608,406 | B2 | 10/2009 | Valkirs et al. |
| 7,739,056 | B2 | 6/2010 | Landfield et al. |
| 7,785,601 | B2 | 8/2010 | Schaebitz et al. |
| 7,851,172 | B2 | 12/2010 | Lovell et al. |
| 7,908,090 | B2 | 3/2011 | Kim et al. |
| 8,211,310 | B2 | 7/2012 | Young et al. |
| 8,257,922 | B2 | 9/2012 | Liew et al. |
| 8,272,518 | B2 | 9/2012 | Fujita et al. |
| 8,349,550 | B2 | 1/2013 | Brady et al. |
| 8,772,042 | B2 | 7/2014 | Yalkinoglu et al. |
| 8,778,616 | B2 | 7/2014 | Ambati et al. |
| 8,828,977 | B2 | 9/2014 | Zahos et al. |
| 9,161,968 | B2 | 10/2015 | Wyss-Coray et al. |
| 9,511,094 | B2 | 12/2016 | Fraser et al. |
| 9,770,486 | B2 | 9/2017 | Wyss-Coray et al. |
| 9,782,457 | B2 | 10/2017 | Chandler et al. |
| 2002/0055158 | A1 | 5/2002 | Greene et al. |
| 2002/0143283 | A1 | 10/2002 | Braverman et al. |
| 2002/0151064 | A1 | 10/2002 | Rothenberg et al. |
| 2003/0139332 | A1 | 7/2003 | Noble et al. |
| 2003/0157687 | A1 | 8/2003 | Greene et al. |
| 2004/0120937 | A1 | 6/2004 | Wilson |
| 2004/0127445 | A1 | 7/2004 | Liew et al. |
| 2004/0141946 | A1 | 7/2004 | Schaebitz et al. |
| 2004/0254152 | A1 | 12/2004 | Monje et al. |
| 2005/0142101 | A1 | 6/2005 | Forssmann et al. |
| 2005/0221348 | A1 | 10/2005 | Ray et al. |
| 2005/0244448 | A1 | 11/2005 | Chen et al. |
| 2006/0031951 | A1 | 2/2006 | Klimanskaya et al. |
| 2006/0094064 | A1 | 5/2006 | Ray et al. |
| 2006/0198851 | A1 | 9/2006 | Basi et al. |
| 2006/0263759 | A1 | 11/2006 | Alves-Filho et al. |
| 2007/0037200 | A1 | 2/2007 | Ray et al. |
| 2007/0155725 | A1 | 7/2007 | Li et al. |
| 2007/0190055 | A1 | 8/2007 | Ambati |
| 2008/0026485 | A1 | 1/2008 | Hueber et al. |
| 2008/0057590 | A1 | 3/2008 | Urdea et al. |
| 2008/0125354 | A1 | 5/2008 | Fields et al. |
| 2009/0143394 | A1 | 6/2009 | Wyss-Coray et al. |
| 2009/0181008 | A1 | 7/2009 | Ray et al. |
| 2009/0209615 | A1 | 8/2009 | Lipton et al. |
| 2009/0239241 | A1 | 9/2009 | Ray et al. |
| 2010/0015235 | A1 | 1/2010 | Watson et al. |
| 2010/0080850 | A1 | 4/2010 | Hubbel et al. |
| 2010/0119496 | A1 | 5/2010 | Wilkison et al. |
| 2010/0124756 | A1 | 5/2010 | Ray et al. |
| 2010/0258496 | A1 | 10/2010 | Hidaka et al. |
| 2010/0310609 | A1 | 12/2010 | Watson et al. |
| 2010/0324079 | A1 | 12/2010 | Ohyagi |
| 2011/0117100 | A1 | 5/2011 | Britschgi et al. |
| 2011/0142848 | A1 | 6/2011 | Chung et al. |
| 2011/0202284 | A1 | 8/2011 | McReynolds et al. |
| 2011/0212854 | A1 | 9/2011 | Ray et al. |
| 2011/0243947 | A1 | 10/2011 | Doody et al. |
| 2012/0095000 | A1 | 4/2012 | Wyss-Coray et al. |
| 2012/0230941 | A1 | 9/2012 | Sing et al. |
| 2013/0040844 | A1 | 2/2013 | Wyss-Coray et al. |
| 2013/0302322 | A1 | 11/2013 | Wong et al. |
| 2014/0011689 | A1 | 1/2014 | Sandip et al. |
| 2014/0121438 | A1 | 5/2014 | Long et al. |
| 2014/0255424 | A1 | 9/2014 | Wyss-Coray et al. |
| 2014/0294724 | A1 | 10/2014 | Chain et al. |
| 2015/0031562 | A1 | 1/2015 | Kantor et al. |
| 2015/0079045 | A1 | 3/2015 | Kong |
| 2015/0157664 | A1 | 6/2015 | Wyss-Coray et al. |
| 2016/0208011 | A1 | 7/2016 | Wyss-Coray et al. |
| 2017/0081415 | A1 | 3/2017 | Wong et al. |
| 2017/0232118 | A1 | 8/2017 | Wyss-Coray et al. |

FOREIGN PATENT DOCUMENTS

| | | |
|---|---|---|
| RU | 2428997 C1 | 9/2011 |
| RU | 2470677 C1 | 12/2012 |
| UA | 35656 C2 | 4/2001 |
| WO | WO 1990011287 | 10/1990 |
| WO | WO 1997038314 | 10/1997 |
| WO | WO 1999006098 | 2/1999 |
| WO | WO 2000062836 | 10/2000 |
| WO | WO 2002006480 A2 | 1/2002 |
| WO | WO 2003006006 | 1/2003 |
| WO | WO 2003020403 | 3/2003 |
| WO | WO 2004019043 | 3/2004 |
| WO | WO 2004060425 | 7/2004 |
| WO | WO 2005052592 A2 | 6/2005 |
| WO | WO 2005106492 A2 | 11/2005 |
| WO | WO 2006102170 A2 | 9/2006 |
| WO | WO 2006133423 A1 | 12/2006 |
| WO | WO 2007059135 A2 | 5/2007 |
| WO | WO 2008014314 | 1/2008 |
| WO | WO 2008146018 | 12/2008 |
| WO | WO 2009023814 A2 | 2/2009 |
| WO | WO 2009055729 A1 | 4/2009 |
| WO | WO 2010017443 | 2/2010 |
| WO | WO 2010041617 | 4/2010 |
| WO | WO 2011094535 A2 | 8/2011 |
| WO | WO 2013142135 A1 | 9/2013 |
| WO | WO 2015081166 A1 | 6/2015 |
| WO | WO 2015088915 A1 | 6/2015 |
| WO | WO 2015161112 A1 | 10/2015 |
| WO | WO 2016187217 A2 | 11/2016 |
| WO | WO 2016205004 A2 | 12/2016 |
| WO | WO 2017120461 A1 | 7/2017 |

OTHER PUBLICATIONS

Anderson et al., "The human plasma proteome: history, character, and diagnostic prospects." Mol Cell Proteomics. Nov. 2002;1(11):845-67.

Baba et al., "Timp-3 deficiency impairs cognitive function in mice." Lab Invest. Dec. 2009;89(12):1340-7.

Berezovskaya et al., "Colony stimulating factor-1 potentiates neuronal survival in cerebral cortex ischemic lesion." Acta Neuropathol. Nov. 1996;92(5):479-86.

Bhattacharya "Placental umbilical cord whole blood transfusion: a safe and genuine blood substitute for patients of the under-resourced world at emergency." J Am Coll Surg. 2005. Submitted 34 pages.

Bhattacharya "Study of the utility of placental cord blood in meeting the transfusion needs of beta-thalassaemic patients" Regional Health Forum, 2008. pp. 16-27.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Borlongan et al., "Central nervous system entry of peripherally injected umbilical cord blood cells is not required for neuroprotection in stroke." Stroke. Oct. 2004;35(10):2385-9.

Bouchard et al. "Aging and brain rejuvenation as systemic events", J. Neurochem. Jan. 2015; 132(1):5-19.

Brew et al., "The tissue inhibitors of metalloproteinases: An ancient family with structural and functional diversity," Biochimica et Biophysica Acta (2010) 1803: 55-71).

(56) References Cited

OTHER PUBLICATIONS

Britschgi et al., "Blood protein signature for the early diagnosis of Alzheimer disease." Arch Neurol. Feb. 2009;66(2):161-5.
Cheung et al., "Serum β-2 microglobulin predicts mortality in people with diabetes." Eur J Endocrinol. May 17, 2013;169(1):1-7.
Conboy et al., "Heterochronic parabiosis for the study of the effects of aging on stem cells and their niches." Cell Cycle. Jun. 15, 2012;11(12):2260-7.
Conboy et al., "Heterochronic parabiosis: historical perspective and methodological considerations for studies of aging and longevity." Aging Cell. Jun. 2013;12(3):525-30.
Conboy et al., "Rejuvenation of aged progenitor cells by exposure to a young systemic environment." Nature. Feb. 17, 2005;433(7027):760-4.
Fedoroff e al., "Role of colony stimulating factor-1 in brain damage caused by ischemic." Neurosci Biobehav Rev. Mar. 1997;21(2):187-91.
Gomez, et al., "Tissue inhibitors of metalloproteinases: structure, regulation and biological functions," European Journal of Cell Biology (1997) 74: 111-22).
Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.
Jha, Alok. "Young blood can reverse some effects of ageing, study finds", The Guardian, Oct. 17, 2012, 4 pages.
Kassiri, et al., "Tissue inhibitor of metalloproteinases (TIMPs) in heart failure," Heart Failure Reviews (2012) 17: 693-706).
Katcher "Studies that shed new light on aging." Biochemistry (Mosc). Sep. 2013;78(9):1061-70.
Komosinkska-Vassev, et al., "Age-and gender-dependent changes in connective tissue remodeling: physiological differences in circulating MMP-3, MMP-10, TIMP-1, and TIMP-2 levels," Gerontology (2011) 57: 44-52).
Krementsov "A Martian Stranded on Earth: Alexander Bogdanov, Blood Transfusions, and Proletarian Science" pp. 57-59,85,86, and 88. University of Chicago Press, Chicago, United States, 2011.
Kwak et al., "Aging, exercise, and extracellular matrix in the heart." J Exerc Rehabil. Jun. 30, 2013;9(3):338-47.
Lee, et al., "Effects of aging on blood brain barrier and matrix metalloproteases following controlled cortical impact in mice," Experimental Neurology (2012) 234: 50-61).
Lin et al., "Discovery of a cytokine and its receptor by functional screening of the extracellular proteome." Science. May 9, 2008;320(5877):807-11.
Loffredo et al., "Growth differentiation factor 11 is a circulating factor that reverses age-related cardiac hypertrophy." Cell. May 9, 2013;153(4):828-39.
Luo et al. "Colony-stimulating factor 1 receptor (CSF1R) signaling in injured neurons facilitates protection and survival.", J. Exp. Med. (2013) 210(1):157-172.
Lysaght et al., "Beta-2 microglobulin removal during continuous ambulatory peritoneal dialysis (CAPD)." Perit Dial Int. 1989;9(1):29-35.
Malkki, H. "Ageing: Could young blood combat age-related cognitive decline?" Nat. Rev. Neurol. Jun. 2014;10(6):307.
Manzo et al., "Role of chemokines and chemokine receptors in regulating specific leukocyte trafficking in the immune/ inflammatory response." Clin Exp Rheumatol. Jul.-Aug. 2003;21(4):501-8.
Mclaurin et al., "Microglial pilgrimage to the brain." Nat Med. Dec. 2010;16(12):1380-1.
Middeldorp et al. "A young systemic environment reverses degeneration in a mouse model of Alzheimer's disease", Neuroscience 2012, Presentation Abstract, Oct. 16, 2012, 2 pages.
Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.

Mizuno e al., "Interleukin-34 selectively enhances the neuroprotective effects of microglia to attenuate oligomeric amyloid-β neurotoxicity." Am J Pathol. Oct. 2011;179(4):2016-27.
Moore et al., "An Alternate Perspective on the Roles of TIMPs and MMPs in Pathology," The American Journal of Pathology (2012) 180: 12-16).
Murphy, "Tissue inhibitors of metalloproteinases," Genome Biology (2011) 12).
Palop et al., "A network dysfunction perspective on neurodegenerative diseases." Nature. Oct. 19, 2006;443(7113):768-73.
Prakasam et al., "Amyloid and Neurodegeneration: Alzheimer's Disease and Retinal Degeneration" Chapter 7, Handbook of Neurochemistry and Molecular Neurobiology, Lajtha ed., 2009, 131-163. (Year: 2009).
Ron-Harel et al. "Age-Dependent Spatial Memory Loss Can Be Partially Restored by Immune Activation", Rejuvenation Resarch (2008), 11(5):903-13.
Royer et al., "A novel antagonist of prostaglandin 02 blocks the locomotion of eosinophils and basophils." Eur J Clin nvesl. Sep. 2008;38(9):663-71.
Schwartz et al. "How Do Immune Cells Support and Shape the Brain in Health, Disease, and Aging?" The Journal of Neuroscience, Nov. 6, 2013, 33(45):17587-96.
Sellebjerg, et al., "Identification of new sensitive biomarkers for the in vivo response to interferon-beta treatment in multiple sclerosis using DNA-array evaluation." Eur J Neurol. Dec. 2009;16(12):1291-8.
Shin et al., "Association of Eotaxin gene family with asthma and serum total IgE." Hum Mol Genet. Jun. 1, 2003;12(11):1279-85.
Skovronsky et al., "Neurodegenerative diseases: new concepts of pathogenesis and their therapeutic implications." Annu Rev Pathol. 2006;1:151-70.
Smith et al., "β2-microglobulin is a systemic pro-aging factor that impairs cognitive function and neurogenesis." Nat Med. Aug. 2015;21(8):932-7.
Stetler-Sstevenson et al., "TIMP-2: an endogenous inhibitor of angiogenesis," Trends in Molecular Medicine (2005) 11: 97-103).
Stetler-Stevenson, "Tissue Inhibitors of Metalloproteinases in Cell Signaling," Science Signaling (2008) 1).
Strobel et al., "Chicago: The Vampire Principle—Young Blood Rejuvenates Aging Brain?", Alzheimer Research Forum (Nov. 2009), p. 1-3.
Stubbs et al., "Indomethacin causes prostaglandin 0(2)-like and eotaxin-like selective responses in eosinophils and basophils." J Bioi Chern. Jul. 19, 2002;277(29):26012-20.
Suzuki et al., "Beta2-microglobulin-selective adsorbent column (Lixelle) for the treatment of dialysis-related amyloidosis." Ther Apher Dial. Feb. 2003;7(1):104-7.
Teixeira, A.L. et al, "Increased serum levels of CCL 11/eotaxin in schizophrenia", Process in Neuro-Psychopharmacology & Biological Psychiatry, vol. 32, No. 3, pp. 710-714, 2008.
Thomson et al. "Young blood for a keener mind", NewScientist (2012), 216(2887):10.
Villeda et al. "The aging systemic milieu negatively regulates neurogenesis and cognitive function", Nature, Aug. 31, 2011, 477(7362):90-4.
Villeda et al. "Young blood reverses age-related cognitive impairments", Neuroscience 2012, Presentation Abstract, Oct. 17, 2012, 2 pages.
Villeda et al. "Young blood reverses age-related impairments in cognitive function and synaptic plasticity in mice", Nat Med. (Jun. 2014), 20(6):659-63.
Villeda et al., "Changes in the systemic milieu modulate neurogenesis during aging" Abstract, 39th Annual Neuroscience Meeting, Chicago, IL, Society for Neuroscience, Oct. 2009, 1-2. (Year: 2009).
Villeda et al., Meeting Date, Past and Future Meetings, 39th Annual Neuroscience Meeting, Society for Neuroscience, 2009, 1. (Year: 2009).
Vincent et al., "Macrophage colony stimulating factor prevents NMDA-induced neuronal death in hippocampal organotypic cultures." J Neurochem. Sep. 2002;82(6):1388-97.
Visse et al. "Matrix Metalloproteinases and Tissue Inhibitors of Metalloproteinases," Circulation Research (2003) 92: 827-39).

(56) References Cited

OTHER PUBLICATIONS

Wang et al., "Expression of colony stimulating factor-1 receptor (CSF-1R) by CNS neurons in mice." J Neurosci Res. Sep. 1, 1999;57(5):616-32.

Wang et al., "Matrix metalloproteinases and their multiple roles in Alzheimer's disease." Biomed Res Int. 2014;2014:908636.

Website document entitled "Plasma Protein Composition" (available at http://www.sigmaaldrich science/metabolomics/enzyme-explorer/learning-center/plasma-blood-proteins/plasma-protein-composition.html). Downloaded from internet Jun. 27, 2017., 3 pages.

Wilson et al., "Beta2-microglobulin as a biomarker in peripheral arterial disease: proteomic profiling and clinical studies." Circulation. Sep. 18, 2007;116(12):1396-403.

Xu, et al., "Matrix Metalloproteinase Inhibitors: A review on Bioanalytical Methods, Pharmacokinetics and Metabolism," Current Drug Metabolism (2011) 12: 395-410).

Yagihashi A. et al., "Macrophage colony stimulating factor (M-CSF) protects spiral ganglion neurons following auditory nerve injury: morphological and functional evidence." Exp Neurol. Mar. 2005;192(1):167-77.

Yamane et al., "CSF-1 receptor-mediated differentiation of a new type of monocytic cell with B cell-stimulating activity: its selective dependence on IL-34." J Leukoc Biol. Jan. 2014;95(1):19-31.

Ye, et al., "Haptoglobin-alpha subunit as potential serum biomarker in ovarian cancer: identification and characterization using proteomic profiling and mass spectrometry." Clinical Cancer Research (Aug. 2003), 9 (8):2904-11.

SFN "Young blood can reverse some effects of ageing, study finds", Author Unknown, Society for Neuroscience, The Observer, Oct. 24, 2012, 2 pages, Retrieved online: http://gonzoj.wordpress.com/tag/society-for-neuroscience/.

Search Report dated Aug. 2, 2017, for related European application No. 14868769.2, 8 pages.

Search Report of related PCT/US2011/022916, dated Oct. 31, 2011, 11 pages.

Search Report of related PCT/US2014/068897, dated Feb. 27, 2015, 11 pages.

Search Report of related PCT/US2016/032907, dated Dec. 1, 2016, 24 pages.

Search Report of related PCT/US2016/036032, dated Feb. 21, 2017, 13 pages.

Search Report of related PCT/US2017/012521, dated Feb. 2, 2017, 12 pages.

Examiner Report of 2016265948, dated May 11, 2018, 6 pages.

Examiner Report of 738184, dated April 6, 2018, 4 pages.

Adachi et al., "Intravascular lymphomatosis: a case report" No Shinkei Geka. Jul. 2001;29(7):659-65. Original in Japanese (English abstract obtained from pubmed).

Allodi "modeling motor neuron resilience in ALS using stem cells" accessed from biorxiv (Year: 2018), 28 pages.

Ameer et al., "A novel immunoadsorption device for removing beta2-microglobulin from whole blood." Kidney Int. Apr. 2001;59(4):1544-50.

Archibald et al., "The retina in Parkinson's disease." Brain. May 2009;132(Pt 5):1128-45.

Cairo CW et al., Drug-Receptor Interactions, Principles of Pharmacology, (2nd ed.), Chapter 1, pp. 3-18 (2008)).

GHR "Parkinson's disease" accessed from ghr.nlm.nih.gov on Mar. 15, 2019 (Year: 2019), 10 pages.

Gilbert et al., "The Role of Inflammation in Parkinson's Disease" Jun. 12, 2018. Accessed from apdaparkinson.org on Nov. 5, 2019. 11 pages.

Giorgetti et al., "beta2-Microglobulin is potentially neurotoxic, but the blood brain barrier is likely to protect the brain from its toxicity." Nephrol Dial Transplant. Apr. 2009;24(4):1176-81.

Kegel "Inflammatory Processes in Huntington's: Researchers Seek to Understand Influence on Disease" accessed from huntingtonsdiseasenews.com on Nov. 5, 2019. (year: 2016) 10 pages.

Longo "Alzheimer's Prevention, Treatment and Research—A Q&A" Stanford Health Now, 2016, 1-2.

Perez-Martinez et al. "Tissue inhibitor of metalloproteinase-2 promotes neuronal differentiation by acting as an anti-mitogenic signal." J Neurosci. May 18, 2005;25(20):4917-29.

Martino et al., "Circulating MicroRNAs Are Not Eliminated by Hemodialysis" (2012) Circulating MicroRNAs Are Not Eliminated by Hemodialysis. PLOS ONE 7(6): e38269.

Mayer et al., "Identification of receptor binding and activation determinants in the N-terminal and N-loop regions of the CC chemokine eotaxin." J Biol Chem. Apr. 27, 2001;276(17):13911-6.

Niezgoda et al., "The effect of cladribine treatment on beta-2 microglobin in the cerebrospinal fluid and serum of patients with multiple sclerosis" Neurol Neurochir Pol. Mar.-Apr. 2000;34(2):281-7. (Abstract).

Politis et al., "Parkinson's disease symptoms: the patient's perspective." Mov Disord. Aug. 15, 2010;25(11):1646-51.

Reitz, "Toward precision medicine in Alzheimer's disease." Ann Transl Med. Mar. 2016;4(6):107.

Shen et al., "CCR3 monoclonal antibody inhibits airway eosinophilic inflammation and mucus overproduction in a mouse model of asthma." Acta Pharmacol Sin. Dec. 2006;27(12):1594-9.

Takeda et al., "CCR3 is a target for age-related macular degeneration diagnosis and therapy." Nature. Jul. 9, 2009;460(7252):225-30.

Wikipedia A "Huntingtin" accessed on Mar. 15, 2019 (excerpt) (Year: 2019).

Wikipedia B "Huntington's disease (Genetics)" accessed Mar. 15, 2019 (excerpt) (Year: 2019).

Zheng et al., "Agonist-selective signaling of G protein-coupled receptor: mechanisms and implications." IUBMB Life. Feb. 2010;62(2):112-9.

Examiner Report of 720949, dated January 18, 2019, 5 pages.

* cited by examiner

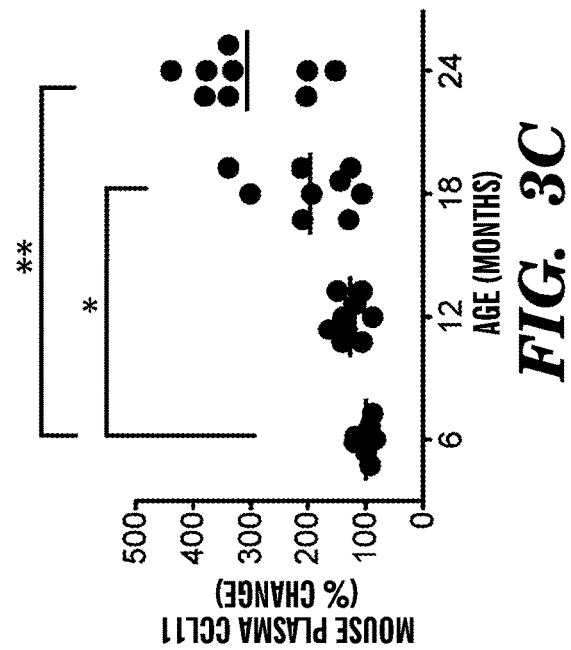
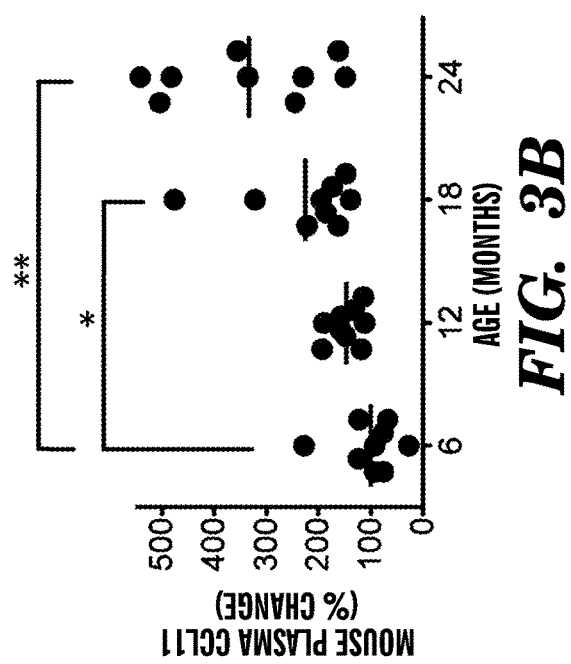
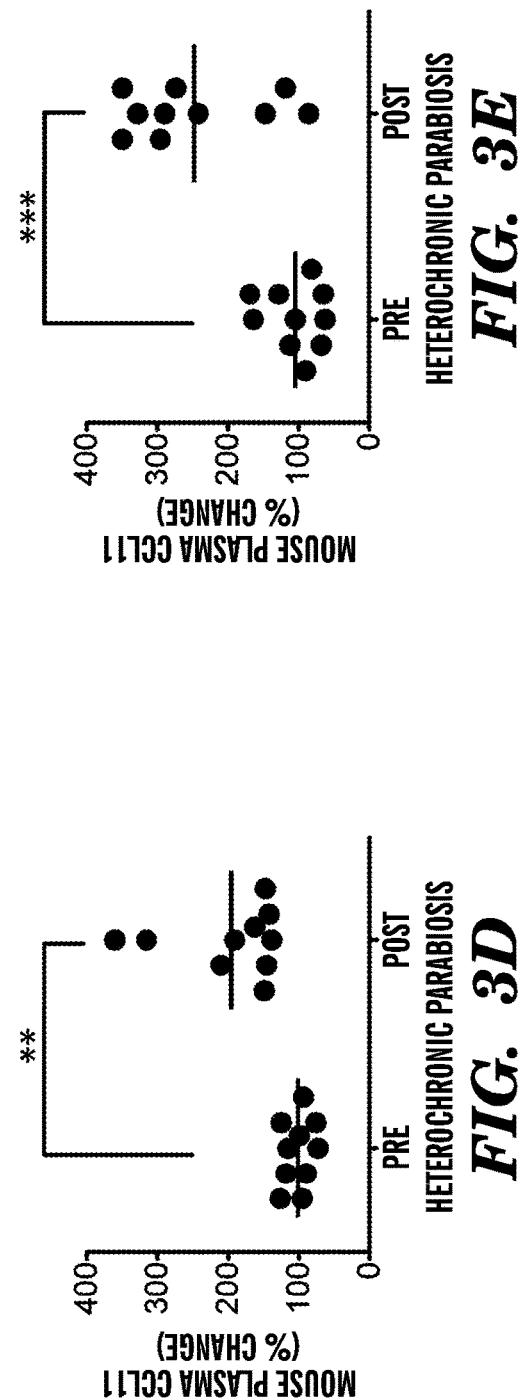

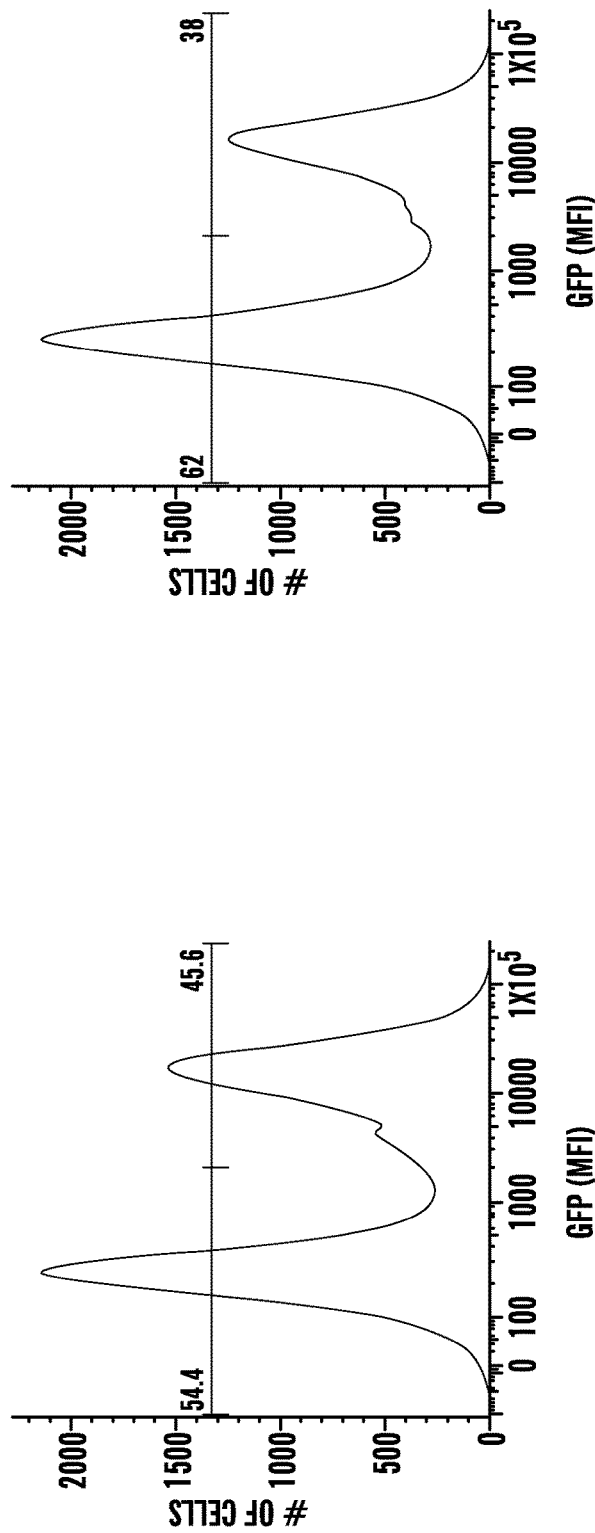
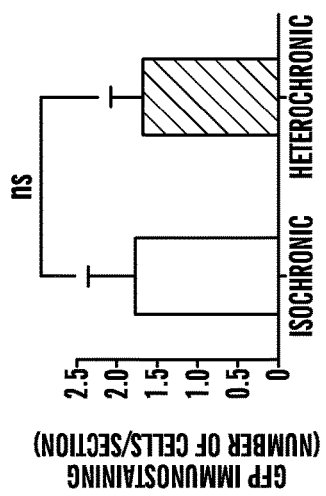
FIG. 8C
FIG. 8D
FIG. 8E

| NAME | SCORE (d) | q-VALUE (%) |
|---|---|---|
| CCL11 | -1.40 | 0 |
| CCL2 | -1.39 | 0 |
| IP-10 | -1.29 | 0 |
| SGOT | -1.12 | 0 |
| HAPTOGLOBIN | -1.10 | 0 |
| OSTEOPONTIN | -1.09 | 0 |
| MIP-2 | -1.08 | 0 |
| vWF | -0.99 | 0 |
| CCL7 | -0.98 | 0 |
| MIP-3β | -0.92 | 0 |
| MIP-1γ | -0.89 | 2.80 |
| TIMP-1 | -0.82 | 2.80 |
| LYMPHOTACTIN | -0.82 | 2.80 |
| β2-MICROGLOBULIN | -0.82 | 2.80 |
| LEPTIN | -0.67 | 7.33 |
| CCL12 | -0.67 | 7.33 |
| MDC | -0.64 | 7.33 |

*FIG. 9A*

| PROTEIN FACTOR | FOLD CHANGE (VERSUS ISOCHRONIC) | |
|---|---|---|
| | YOUNG HETEROCHRONIC | OLD HETEROCHRONIC |
| CD40 | n.c. | -1.4±0.1 |
| CCL11 | 2.1±0.3 | n.c. |
| GCP-2 | 3.5±0.4 | n.c. |
| HAPTOGLOBIN | 8.5±0.6 | -1.4±0.1 |
| IL-11 | 8.5±1.4 | 4.6±1.5 |
| IL-1α | 6.5±1.1 | -1.4±0.1 |
| IL-5 | 2.2±0.2 | -1.6±0.04 |
| IL-7 | 6.5±1.0 | n.c. |
| KC/GROα | 7.3±1.1 | n.c. |
| CCL2 | 2.3±0.2 | n.c. |
| CCL12 | 2.1±0.1 | n.c. |
| MIP-1β | 2.9±0.3 | n.c. |
| MIP-3β | 2.2±0.1 | n.c. |
| MYOGLOBIN | 2.9±0.6 | n.c. |
| β2-MICROGLOBULIN | 17.7±1.7 | n.c. |
| MPO | 2.8±0.3 | n.c. |

*FIG. 9C*

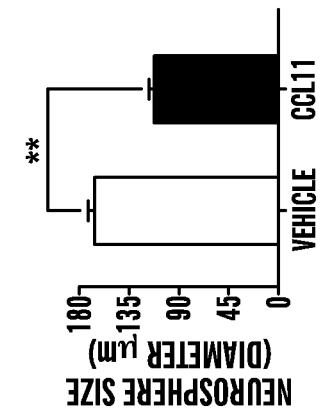
FIG. 12E
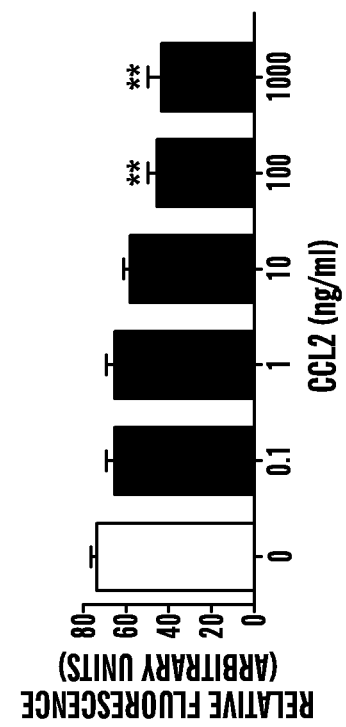
FIG. 12F
FIG. 12H
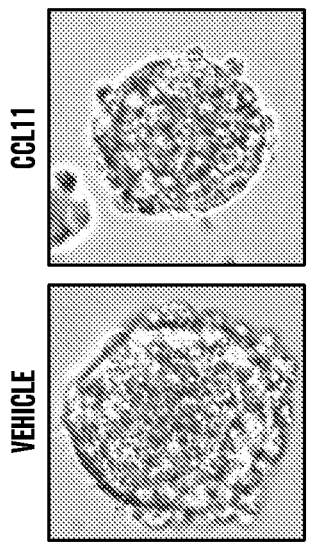
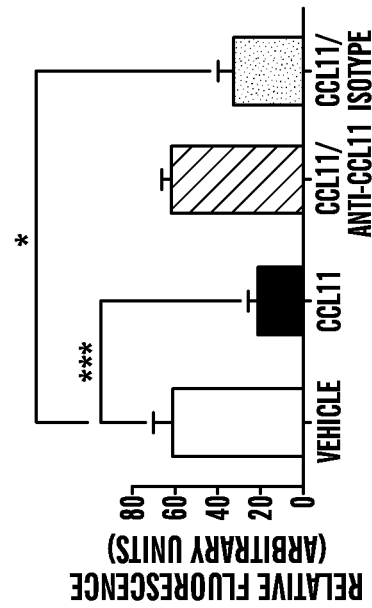
FIG. 12G

METHODS OF TREATING COGNITIVE SYMPTOMS OF AN AGING-ASSOCIATED IMPAIRMENT BY MODULATING C-C CHEMOKINE RECEPTOR TYPE 3 (CCR3)

CROSS-REFERENCE TO RELATED APPLICATIONS

This application claims priority to U.S. application Ser. No. 14/991,813 filed on Jan. 8, 2016; which application is a continuation-in-part application of U.S. application Ser. No. 14/280,939 filed May 19, 2014; which application is a Continuation Application of U.S. application Ser. No. 13/575,437, filed on Oct. 9, 2012 and now abandoned; which application is a 35 U.S.C. § 371 National Phase Entry Application of International Application Serial No. PCT/US2011/022916, filed Jan. 28, 2011, which designates the United States, and which claims benefit under 35 U.S.C. § 119(e) of the U.S. Provisional Application Ser. No. 61/298,998, filed on Jan. 28, 2010; the disclosures of which applications are herein incorporated by reference in their entirety.

GOVERNMENT RIGHTS

This invention was made with Government support under contract AG027505 and OD000392 awarded by the National Institutes of Health. The Government has certain rights in the invention.

INTRODUCTION

Aging in an organism is accompanied by an accumulation of changes over time. In the nervous system, aging is accompanied by structural and neurophysiological changes that drive cognitive decline and susceptibility to degenerative disorders in healthy individuals. (Hedden & Gabrieli, "Insights into the ageing mind: a view from cognitive neuroscience," Nat. Rev. Neurosci. (2004) 5: 87-96; Raz et al., "Neuroanatomical correlates of cognitive aging: evidence from structural magnetic resonance imaging," Neuropsychology (1998) 12:95-114; Mattson & Magnus, "Ageing and neuronal vulnerability," Nat. Rev. Neurosci. (2006) 7: 278-294; and Rapp & Heindel, "Memory systems in normal and pathological aging," Curr. Opin. Neurol. (1994) 7:294-298). Included in these changes are synapse loss and the loss of neuronal function that results. Thus, although significant neuronal death is typically not observed during the natural aging process, neurons in the aging brain are vulnerable to sub-lethal age-related alterations in structure, synaptic integrity, and molecular processing at the synapse, all of which impair cognitive function.

In addition to the normal synapse loss during natural aging, synapse loss is an early pathological event common to many neurodegenerative conditions, and is the best correlate to the neuronal and cognitive impairment associated with these conditions. Indeed, aging remains the single most dominant risk factor for dementia-related neurodegenerative diseases such as Alzheimer's disease (AD) (Bishop et al., "Neural mechanisms of ageing and cognitive decline," Nature (2010) 464: 529-535 (2010); Hedden & Gabrieli, "Insights into the ageing mind: a view from cognitive neuroscience," Nat. Rev. Neurosci. (2004) 5:87-96; Mattson & Magnus, "Ageing and neuronal vulnerability," Nat. Rev. Neurosci. (2006) 7:278-294).

As human lifespan increases, a greater fraction of the population suffers from aging-associated cognitive impairments, making it crucial to elucidate means by which to maintain cognitive integrity by protecting against, or even counteracting, the effects of aging (Hebert et al., "Alzheimer disease in the US population: prevalence estimates using the 2000 census," Arch. Neurol. (2003) 60:1119-1122; Bishop et al., "Neural mechanisms of ageing and cognitive decline," Nature (2010) 464:529-535).

SUMMARY

Methods of treating an adult mammal for an aging-associated impairment are provided. Aspects of the methods include modulating CCR3, e.g., via modulation of eotaxin-1/CCR3 interaction, in the mammal in a manner sufficient to treat the mammal for the aging-associated impairment. A variety of aging-associated impairments may be treated by practice of the methods, which impairments include cognitive impairments.

BRIEF DESCRIPTION OF THE FIGURES

FIG. 1A shows a schematic of the three combinations of mice used in isochronic and heterochronic pairings. FIG. 1B shows quantification of neurogenesis in the young DG after parabiosis. Data are from 12 mice for isochronic and 10 mice for heterochronic groups (5-7 sections per mouse). FIG. 1C shows quantification of neurogenesis in the old DG after parabiosis. Data are from 6 mice for isochronic and 12 mice for heterochronic groups (5-7 sections per mouse; **, $P<0.01$). e, High magnification view of neurite arbors from Doublecortin-positive neurons from young (scale bar: 50 µm) and old (scale bar: 25 µm) parabiotic pairings. FIG. 1D shows quantification of average neurite length from young isochronic and heterochronic parabionts. The length of the longest visible neurite was measured in 250 neurons (measured in random fields across 5 sections per mouse). FIG. 1E shows quantification of average neurite length from old isochronic and heterochronic parabionts as described for young mice. Mean+SEM; *, $P<0.05$; **, $P<0.01$ t-test.

FIG. 2A shows quantification of neurogenesis in the young DG after plasma injection. Data are from 7-8 mice per group (5-7 sections per mouse). FIGS. 2B and 2C show experiments where synaptic plasticity of young isochronic and heterochronic parabionts was examined after five weeks of parabiotic pairing in hippocampal slices by extracellular electrophysiological recordings using a long-term potentiation (LTP) paradigm. FIG. 2B shows representative electrophysiological profiles collected from individual young (3 months) isochronic and heterochronic parabionts during LTP recordings from the DG. FIG. 2C shows that LTP levels recorded from the DG were lower in the hippocampus of young heterochronic (100.6±34.3%) versus young isochronic (168.5±15.8%) parabionts following 40 minutes after induction. Data are from 4-5 mice per group. FIGS. 2D and 2E show how spatial learning and memory was assessed using the radial arm water maze (RAWM) paradigm in young (3 months) adult male mice injected intravenously with plasma isolated from young (3-4 months) and old (18-20 months) mice every three days for 24 days. FIG. 2D shows a schematic of the RAWM paradigm. The goal arm location containing the platform remains constant, while the start arm is changed during each trial. On day one during the training phase, mice are trained for 15 trials, with trials alternating between visible (white) and hidden (shaded) platform. On day two during the testing phase, mice are tested for 15 trials with the hidden (shaded) platform. Entry into an incorrect arm is scored as an error, and errors are averaged over training blocks (three consecutive trials). FIG. 2E shows how learning and memory deficits were quantified as the number of entry arm errors made prior to finding the target platform. Data are from 7-8 mice per group. Mean±SEM; *, P<0.05; **, P<0.01, t-test (2A), ANOVA, Tukey's post-hoc test (2E).

FIGS. 3A-3I show that systemic chemokine levels increase during normal aging and heterochronic parabiosis and correlate with the age-dependent decrease in neurogenesis. FIG. 3A shows a Venn diagram outlining the results from the normal aging and parabiosis proteomic screens. The seventeen blood borne factors whose levels increased with aging and correlated strongest with the age-related decline in neurogenesis are shown in left side circle, the fourteen blood borne factors that increased between young isochronic and young heterochronic parabionts are shown in right side circle, and the five factors elevated in both screens are shown in the intersection in light grey area. (5-6 animals per age group were used) FIGS. 3B-3E show changes in plasma concentrations for CCL2 (3B, 3D) and CCL11 (3C, 3E) with age (3B, 3C) and from an independent proteomic screen in young heterochronic parabionts pre- and post-parabiotic pairing (3D, 3E). FIGS. 3F-3I show changes in concentrations for CCL2 (3F, 3H) and CCL11 (3G, 3I) in healthy, cognitively normal human subjects in plasma with age (3F, 3G) and in CSF between young (20-45 years) and old (65-90 years) (3H, 3I). Dot plots with mean; *, P<0.05; , P<0.01; *, P<0.001 t-test (c,d), ANOVA, Tukey's post-hoc test (3A, 3B), and Mann-Whitney U Test (3H, 3I).

FIG. 4A shows an experiment where Dcx-luc reporter mice (2-3 months) were injected with either recombinant murine CCL11 or PBS (vehicle) every other day for four days (7 mice per group). Bioluminescence was recorded in living mice at days zero and four, and representative images are shown for each treatment group. FIG. 4B shows results when bioluminescence was quantified as photons/s/cm2/steradian and differences expressed as changes in fold-induction between day zero and four. FIG. 4C shows quantification of neurogenesis in the DG after systemic drug administration after an independent cohort of 3-month-old wild type male mice was injected intraperitoneally with recombinant murine CCL11 or vehicle alone, and in combination with an anti-CCL11 neutralizing antibody or an isotype control antibody four times over ten days (6-10 mice per group). FIG. 4D shows quantification of the relative number of BrdU and NeuN double positive cells compared to the total number of BrdU positive cells in the DG mice that were systemically administered with either recombinant murine CCL11 or vehicle alone from the group above were injected with BrdU daily for three days prior to sacrifice. FIGS. 4E-4F show quantification of neurogenesis in the DG after systemic and stereotaxic drug administration. Data are from 3-10 young adult mice (2-3 months) per group (5 sections per mouse) after young adult mice were given unilateral stereotaxic injections of either anti-CCL11 neutralizing antibody or an isotype control antibody followed by systemic injections with either recombinant CCL11 or PBS. FIG. 4G shows how spatial learning and memory was assessed using the RAWM paradigm in young adult male mice (3 months) injected with recombinant murine CCL11 or PBS (vehicle) every three days for five weeks. Cognitive deficits were quantified as the number of entry arm errors made prior to finding the target platform. All the histological and behavioral assessments were carried out by investigators blinded to the treatment of the mice. Data is represented as Mean±SEM; *, P<0.05; **, P<0.01; t-test (4B, 4D, 4E, 4F), ANOVA, Dunnett's or Tukey's post-hoc test (4C, 4G).

FIGS. 5A-5D show quantification of age-related cellular changes in the adult DG. Data are from 5-10 mice per age group (5-7 sections per mouse), each dot represents the mean number per mouse Animals were given 6 days of BrdU injections and euthanized 21 days following the last injection. FIG. 5C shows age-related increase of relative immunoreactivity to CD68, a marker for microglia activation. FIG. 5D shows that GFAP reactivity did not significantly change with age. Dot plots with mean; ***, P<0.001, ANOVA, Dunnett's post-hoc test.

In FIG. 6A synaptic plasticity of normal aging animals was examined in hippocampal slices by extracellular electrophysiological recordings using a long-term potentiation (LTP) paradigm. LTP levels recorded from the DG were lower in the hippocampus of old (100.25±14.0%, n=7) versus young (201.1±40.6%, n=6) animals following 40 minutes after induction. FIG. 6B shows how spatial learning and memory was assessed during normal aging in young (2-3 months) versus old (18-20 months) adult animals (7-8 057131/6 male mice per group). Old mice demonstrate impaired learning and memory for platform location during the testing phase of the task. Cognitive deficits were quantified as the number of entry arm errors made prior to finding the target platform. All data is represented as Mean±SEM; *, P<0.05; **, P<0.01; ANOVA, Tukey's post-hoc test.

FIG. 7A shows quantification of proliferation in the young DG after parabiosis. Data are from 8 mice for isochronic and 6 mice for heterochronic groups. FIG. 7B shows quantification of proliferation in the aged DG after parabiosis. Data are from 4 mice for isochronic and 6 mice for heterochronic groups. Sox2 immunostaining was also performed for young (3-4 months) isochronic and heterochronic parabionts. FIG. 7C shows quantification of Sox2-positive progenitor cells in the young DG after parabiosis. Data are from 8 mice for isochronic and 6 mice for heterochronic groups. FIGS. 7D and 7E show quantification of neurogenesis (Dcx, Doublecortin-positive cells) in the DG during normal aging and after isochronic (Iso) or heterochronic (Het) parabiosis. 7A data are from 10 normal aged (18 months old) mice, 6 isochronic parabionts (18-20 months old) and 12 heterochronic parabionts (18-20 months old). 7F shows quantification of neurite length during normal aging and after parabiosis in Dcx-positive cells. Dendritic length remained unchanged between unpaired normal aged animals and isochronic parabiotic animals. All data are from 5-7 sections per mouse; bars are mean±SEM; * P<0.05; ** P<0.01; n.s., not significant; t-test.

FIGS. 8A-8E show that circulatory system is shared between animals during parabiosis. FIGS. 8A-8D show a subset of four parabiotic pairs were generated by joining young (2-3 months old) actin-GFP transgenic with young (2-3 months old) and aged (18 months old) non-transgenic mice. Blood was isolated two weeks after surgery and flow cytometric analysis was done on fixed and permeabilized blood cells. Representative flow-cytometry plots demonstrate the frequency of GFP-positive cells in a GFP-transgenic (tg) parabiont (a,c) and wild-type (wt) parabiont (8B, 8D) at the time of sacrifice. MFI, mean fluorescence intensity. FIG. 8E shows quantification of GFP-positive cells in the DG of the hippocampus in young and aged wild-type parabionts after parabiosis with young actin-GFP-positive parabionts. 5 sections per mouse; bars are mean±SEM; n.s., not significant; t-test.

FIGS. 9A-9C show that changes in concentrations of selected secreted plasma proteins correlate with declining neurogenesis in aging and heterochronic parabiosis. FIG. 9A shows an analysis of plasma protein correlations with decreased neurogenesis in the aging mouse samples using the Significance Analysis of Microarray software (SAM 3.00 algorithm). SAM assigns d-scores to each gene or protein on the basis of a multi-comparison analysis of expression changes and indicates significance by q-value. FIG. 9B shows unsupervised clustering of secreted signaling factors that were significantly associated with age-related decreased neurogenesis with a false discovery rate of 7.34% or less (SAM, q 7.34). Mouse age groups are indicated at the top of the node map as boxes in which youngest ages are tan and oldest ages are red. Thus cluster analysis of systemic factors associated with decreased neurogenesis also produce a reasonable separation of samples by age. Color shades in the node map indicate higher (purple) or lower (green) relative plasma concentrations. FIG. 9C shows quantitative fold changes in soluble signaling factors between isochronic versus heterochronic parabiotic groups. Color shades indicate increases (darker gray scale) and decreases (lighter grey scale) in relative plasma concentrations (mean±SEM of fold changes observed with parabiosis; n.c. denotes no significant change).

FIG. 10A shows that a significant increase above basal CCL11 plasma levels was measured in mice treated systemically with recombinant CCL11, but no relative change was observed in animals receiving PBS. Blood was collected by mandibular vein bleed prior to systemic drug administration and by intracardial bleed at time of sacrifice using EDTA as an anticoagulant. Plasma was generated by centrifugation of blood. Samples were diluted 1:10 and CCL11 was detected by Quantikine ELISA following the manufacturer's manual (R&D Systems). BrdU immunostaining was performed in the DG for each treatment group. FIG. 10B shows quantification of BrdU-positive cells in the DG after systemic drug administration. Data are from 5-10 mice per group (5 sections per mouse). Confocal microscopy images from the subgranular zone of the DG of brain sections immunostained for BrdU in combination with GFAP was also performed for both treatment groups. FIG. 10C shows quantification of the relative number of BrdU and GFAP double positive cells out of all BrdU-positive cells in the DG after systemic CCL11 administration. Data are from 5 mice per group (3 sections per mouse). Bars show mean±SEM; *, P<0.05; **, P<0.01; n.s., not significant; t-test (10C) or ANOVA, Dunnet's post-hoc test (10A, 10B).

FIGS. 11A-11O show that systemic administration of MCSF does not alter neurogenesis in the DG of young animals. FIGS. 11A and 11B show a comparison of plasma concentrations for MCSF in normal aged (6, 12, 18 and 24 months old) (11A) and young heterochronic parabionts pre and post parabiotic pairing (11B). Young adult male mice (2-3 months old) were injected with either recombinant MCSF alone or PBS as a vehicle control through intraperitoneal injections every three days for ten days. Neurogenesis was analyzed by immunostaining for Dcx.

FIGS. 12A-12H show that age-related blood borne factors, including CCL11 and CCL2, inhibit NPC function and neural differentiation in vitro. FIG. 12A shows an experiment where primary NPCs were exposed to serum isolated from young (2-3 months) or old (18-22 months) mice for four days in culture under self-renewal conditions. The number of neurospheres formed in the presence of old serum was decreased compared to neurospheres formed in the presence of young serum. FIG. 12B shows a dose-dependent decrease in the number of neurospheres formed from primary mouse NPCs after exposure to murine recombinant CCL11 for four days in culture under self-renewal conditions. FIG. 12C shows decrease in neurosphere formation after exposure to murine recombinant CCL11 compared with PBS (vehicle) control is rescued by addition of anti-CCL11 neutralizing antibody but not by a non-specific isotype control antibody. FIG. 12D shows a decrease in the number of neurospheres formed from primary mouse NPCs after exposure to murine recombinant CCL2 is rescued by addition of anti-CCL2 neutralizing antibody. FIGS. 12E-F show decreased neurosphere size and quantitation thereof after exposure to CCL11. FIG. 12G shows a quantification of decreased neuronal differentiation as a function of reduced expression of Dcx promoter-controlled eGFP in stably transfected human derived NTERA cells after exposure to human recombinant CCL11 (12G) or CCL2 (12H), compared with PBS (vehicle) as a control. FIG. 12G shows that decreased neuronal differentiation is rescued by addition of anti-CCL11 neutralizing antibody but not by a non-specific isotype control antibody. FIG. 12H shows quantification of dose dependent decrease in neuronal differentiation after exposure to human recombinant CCL2. Human NTERA-EGFP reporter cells were cultured under differentiation conditions (RA, retinoic acid) for 12 days and relative Dxc reporter gene activity was measured as fluorescence intensity. In vitro data are representative of three independent experiments done in triplicate. Bars are mean±SEM; *, P<0.05, , P<0.01, *, P<0.001, t-test (a,f) or ANOVA, Dunnett's post-hoc test (12B-12D, 12G, 12H).

DETAILED DESCRIPTION

Figure 1A:
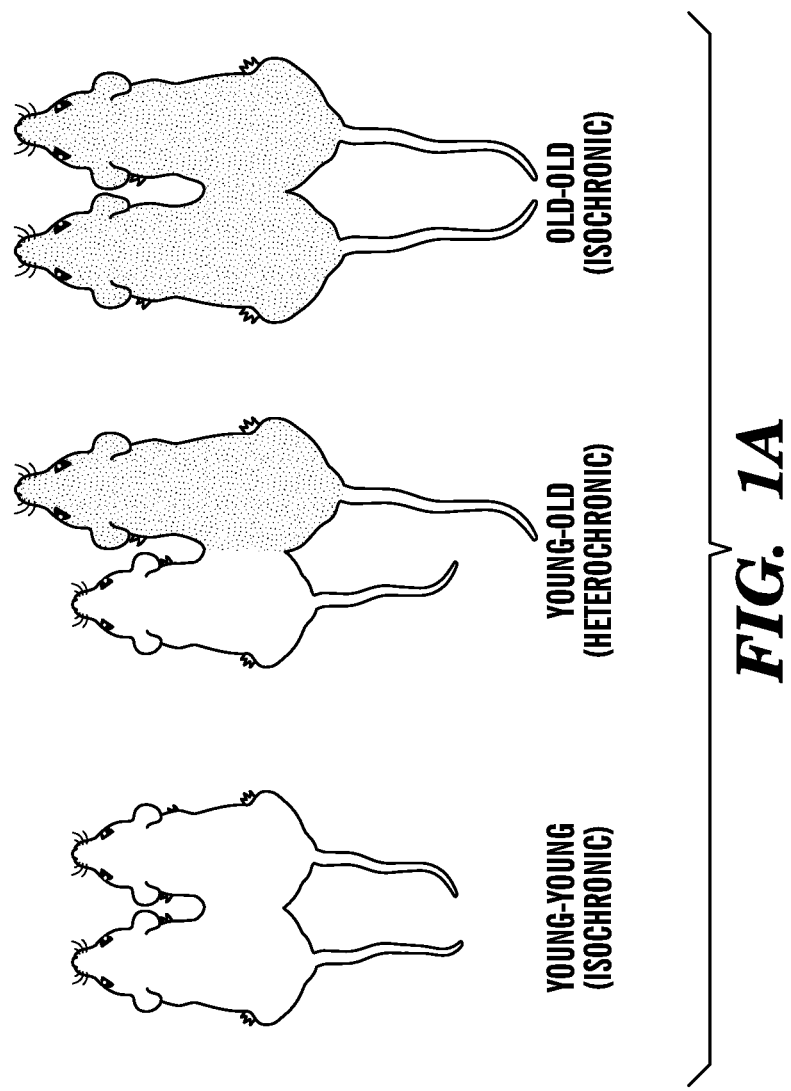
FIGS. 1A-1E show that heterochronic parabiosis reduces adult neurogenesis in young animals while increasing neurogenesis in aged mice.

Methods of treating an adult mammal for an aging-associated impairment are provided. Aspects of the methods include modulating CCR3, e.g., via modulating eotaxin-1/CCR3 interaction, in the mammal in a manner sufficient to treat the mammal for the aging-associated impairment. A variety of aging-associated impairments may be treated by practice of the methods, which impairments include cognitive impairments.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

As summarized above, aspects of the invention include methods of treating an aging-associated impairment in an adult mammal. The aging-associated impairment may manifest in a number of different ways, e.g., as aging-associated cognitive impairment and/or physiological impairment, e.g., in the form of damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone; in the form of decreased neurogenesis, etc.

In some embodiments, the aging-associated impairment is an aging-associated impairment in cognitive ability in an individual, i.e., an aging-associated cognitive impairment. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. Aging-associated cognitive impairments include impairments in cognitive ability that are typically associated with aging, including, for example, cognitive impairment associated with the natural aging process, e.g., mild cognitive impairment (M.C.I.), and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington's disease, amyotrophic lateral sclerosis, multiple sclerosis, glaucoma, myotonic dystrophy, vascular dementia, and the like.

By "treatment" it is meant that at least an amelioration of one or more symptoms associated with an aging-associated impairment afflicting the adult mammal is achieved, where amelioration is used in a broad sense to refer to at least a reduction in the magnitude of a parameter, e.g., a symptom associated with the impairment being treated. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

In some instances where the aging-associated impairment is aging-associated cognitive decline, treatment by methods of the present disclosure slows, or reduces, the progression of aging-associated cognitive decline. In other words, cognitive abilities in the individual decline more slowly, if at all, following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from aging-associated cognitive decline is halted following treatment by the disclosed methods. As another example, cognitive decline in an individual, e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than they were prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In some instances, treatment of an adult mammal in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional, e.g., in the form of enhanced neurogenesis.

As summarized above, methods described herein are methods of treating an aging-associated impairment, e.g., as described above, in an adult mammal. By adult mammal is meant a mammal that has reached maturity, i.e., that is fully developed. As such, adult mammals are not juvenile. Mammalian species that may be treated with the present methods include canines and felines; equines; bovines; ovines; etc., and primates, including humans. The subject methods, compositions, and reagents may also be applied to animal models, including small mammals, e.g., murine, lagomorpha, etc., for example, in experimental investigations. The discussion below will focus on the application of the subject methods, compositions, reagents, devices and kits to humans, but it will be understood by the ordinarily skilled artisan that such descriptions can be readily modified to other mammals of interest based on the knowledge in the art.

The age of the adult mammal may vary, depending on the type of mammal that is being treated. Where the adult mammal is a human, the age of the human is generally 18 years or older. In some instances, the adult mammal is an individual suffering from or at risk of suffering from an aging-associated impairment, such as an aging-associated cognitive impairment, where the adult mammal may be one that has been determined, e.g., in the form of receiving a diagnosis, to be suffering from or at risk of suffering from an aging-associated impairment, such as an aging-associated cognitive impairment. The phrase "an individual suffering from or at risk of suffering from an aging-associated cognitive impairment" refers to an individual that is about 50 years old or older, e.g., 60 years old or older, 70 years old or older, 80 years old or older, and sometimes no older than 100 years old, such as 90 years old, i.e., between the ages of about 50 and 100, e.g., 50, 55, 60, 65, 70, 75, 80, 85 or about 90 years old. The individual may suffer from an aging associated condition, e.g., cognitive impairment, associated with the natural aging process, e.g., M.C.I.

Alternatively, the individual may be 50 years old or older, e.g., 60 years old or older, 70 years old or older, 80 years old or older, 90 years old or older, and sometimes no older than 100 years old, i.e., between the ages of about 50 and 100, e.g., 50, 55, 60, 65, 70, 75, 80, 85, 90, 95 or about 100 years old, and has not yet begun to show symptoms of an aging associated condition, e.g., cognitive impairment. In yet other embodiments, the individual may be of any age where the individual is suffering from a cognitive impairment due to an aging-associated disease, e.g., Alzheimer's disease, Parkinson's disease, frontotemporal dementia, Huntington's disease, amyotrophic lateral sclerosis, multiple sclerosis, glaucoma, myotonic dystrophy, dementia, and the like. In some instances, the individual is an individual of any age that has been diagnosed with an aging-associated disease that is typically accompanied by cognitive impairment, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like, where the individual has not yet begun to show symptoms of cognitive impairment.

As summarized above, aspects of the methods include modulating CCR3. By modulating CCR3 is meant changing its activity in a manner sufficient to treat the mammal for the target aging-associated impairment. Modulating may be accomplished in a variety of different ways, e.g., by changing the ability of CCR3 to interact with one or of its ligands, by changing the expression level of CCR3, etc., as described in greater detail below. In some instances, modulating CCR3 including modulating eotaxin-1/CCR3 interaction in the mammal in a manner sufficient to treat the aging impairment in the mammal, e.g., as described above. By modulating eotaxin-1/CCR3 interaction is meant changing the interaction of eotaxin-1 (i.e., C—C motif chemokine 11, CCL11, eosinophil chemotactic protein) with CCR3 (i.e., C—C chemokine receptor type 3, CD193) in a manner sufficient to achieve the desired treatment. The interaction of eotaxin-1 with CCR3 may be changed using a variety of different approaches, e.g., as described below, including interfering with binding of eotaxin-1 and CCR3, reducing the level of active eotaxin-1 and/or CCR3, etc.

In some instances, the eotaxin-1/CCR3 interaction is modulated by reducing active systemic eotaxin-1 in the mammal. By reducing active systemic eotaxin-1 is meant lowering the amount or level of active eotaxin-1 that is systemically present in (i.e., in the circulatory system of) the mammal, such as the amount of active extracellular eotaxin-1 that is present in the cardiovascular system of the mammal. While the magnitude of the reduction may vary, in some instances the magnitude is 2-fold or greater, such as 5-fold or greater, including 10-fold or greater, e.g., 15-fold or greater, 20-fold or greater, 25-fold or greater (as compared to a suitable control), where in some instances the magnitude is such that the amount of detectable active (e.g., free) eotaxin-1 in the circulatory system of the individual is 50% or less, such as 25% or less, including 10% or less, e.g., 1% or less, relative to the amount that was detectable prior to intervention according to the invention, and in some instances the amount is undetectable following intervention.

The eotaxin-1 level may be reduced using any convenient protocol. In some embodiments, the eotaxin-1 level is reduced by administering to the mammal an effective amount of an active system eotaxin-1 reducing agent, i.e., an agent whose administration results in the reduction of active eotaxin-1 (e.g., eotaxin-1 that can bind to CCR3) that is systemically present in the mammal. As such, in practicing methods according to these embodiments of the invention, an effective amount of the active agent, e.g., eotaxin-1 modulatory agent, is provided to the adult mammal.

Depending on the particular embodiments being practiced, a variety of different types of active agents may be employed. In some instances, the agent is an agent that modulates, e.g., inhibits, eotaxin-1 activity by binding to eotaxin-1 and/or inhibiting binding of eotaxin-1 to a receptor therefore, e.g., CCR3. For example, agents that bind to eotaxin-1 and inhibit its activity are of interest. In certain of these embodiments, the administered active agent is an eotaxin-1 specific binding member. In general, useful eotaxin-1 specific binding members exhibit an affinity (Kd) for a target eotaxin-1, such as human eotaxin-1, that is sufficient to provide for the desired reduction in aging associated impairment eotaxin-1 activity. As used herein, the term "affinity" refers to the equilibrium constant for the reversible binding of two agents; "affinity" can be expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of a specific binding member to a target protein can be, for example, from about 100 nanomolar (nM) to about 0.1 nM, from about 100 nM to about 1 picomolar (pM), or from about 100 nM to about 1 femtomolar (fM) or more. The term "binding" refers to a direct association between two molecules, due to, for example, covalent, electrostatic, hydrophobic, and ionic and/or hydrogen-bond interactions, including interactions such as salt bridges and water bridges. In some embodiments, the antibodies bind human eotaxin-1 with nanomolar affinity or picomolar affinity. In some embodiments, the antibodies bind human eotaxin-1 with a Kd of less than about 100 nM, 50 nM, 20 nM, 20 nM, or 1 nM. In some embodiments, the affinity between the binding member active agent in a binding complex with eotaxin-1 is characterized by a $K_d$ (dissociation constant) of $10^{-6}$ M or less, such as $10^{-7}$ M or less, including $10^{-8}$ M or less, e.g., $10^{-9}$ M or less, $10^{-19}$ M or less, $10^{-11}$ M or less, $10^{-12}$ M or less, $10^{-13}$ M or less, $10^{-14}$ M or less, including $10^{-15}$ M or less.

Examples of eotaxin-1 specific binding members include eotaxin-1 antibodies and binding fragments thereof. Non-limiting examples of such antibodies include antibodies directed against any epitope of eotaxin-1. Also encompassed are bispecific antibodies, i.e., antibodies in which each of the two binding domains recognizes a different binding epitope. Cloning of human eotaxin-1 was reported in Ponath et al., "Cloning of the human eosinophil chemoattractant, eotaxin: expression, receptor binding, and functional properties suggest a mechanism for the selective recruitment of eosinophils," J. Clin. Invest. (1996) 97: 604-612. The amino acid sequence of human eotaxin-1 is MKVSAALLWL LLIAAAFSPQ GLAGPASVPT TCCFNLANRK IPLQR-LESYR RITSGKCPQK AVIFKTKLAK DICADPKKKW VQDSMKYLDQ KSPTPKP (SEQ ID NO:01).

Antibody specific binding members that may be employed include full antibodies or immunoglobulins of any isotype, as well as fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the term are Fab', Fv, F(ab')2, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies that may be used in connection with the present disclosure thus can encompass monoclonal antibodies, polyclonal antibodies, bispecific antibodies, Fab antibody fragments, F(ab)2 antibody fragments, Fv antibody fragments (e.g., VH or VL), single chain Fv antibody fragments and dsFv antibody fragments. Furthermore, the antibody molecules may be fully human antibodies, humanized antibodies, or chimeric antibodies. In some embodiments, the antibody molecules are monoclonal, fully human antibodies.

The antibodies that may be used in connection with the present disclosure can include any antibody variable region, mature or unprocessed, linked to any immunoglobulin constant region. If a light chain variable region is linked to a constant region, it can be a kappa chain constant region. If a heavy chain variable region is linked to a constant region, it can be a human gamma 1, gamma 2, gamma 3 or gamma 4 constant region, more preferably, gamma 1, gamma 2 or gamma 4 and even more preferably gamma 1 or gamma 4.

In some embodiments, fully human monoclonal antibodies directed against eotaxin are generated using transgenic mice carrying parts of the human immune system rather than the mouse system.

Minor variations in the amino acid sequences of antibodies or immunoglobulin molecules are encompassed by the present invention, providing that the variations in the amino acid sequence maintain at least 75%, e.g., at least 80%, 90%, 95%, or 99% of the sequence. In particular, conservative amino acid replacements are contemplated. Conservative replacements are those that take place within a family of amino acids that are related in their side chains. Whether an amino acid change results in a functional peptide can readily be determined by assaying the specific activity of the polypeptide derivative. Fragments (or analogs) of antibodies or immunoglobulin molecules, can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Sequence motifs and structural conformations may be used to define structural and functional domains in accordance with the invention.

Specific examples of antibody agents that may be employed to reduce the level of active systemic eotaxin-1 include, but are not limited to: bertilimumab (i.e., iCo-008 or CAT-213) as further described in Main et al., "A Potent Human Anti-Eotaxin1 Antibody, CAT-213: Isolation by Phage Display and in Vitro and in Vivo Efficacy," JPET (2006) 319: 1395-1404; MAB320, AF-320-NA and MAB3201 from R & D Systems; ANT-126 available from Prospec; as well as the antibodies described in U.S. Pat. Nos. 6,946,546 and 7,323,311; the disclosures of which are herein incorporated by reference.

Eotaxin-1 binding agents that may be employed also include small molecules that bind to the eotaxin-1 and inhibit its activity, i.e., small molecule eotaxin-1 antagonists. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In some instances, the agent modulates expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of an eotaxin-1 protein. Inhibition of eotaxin-1 protein expression may be accomplished using any convenient means, including use of an agent that inhibits eotaxin-1 protein expression, such as, but not limited to: RNAi agents, antisense agents, agents that interfere with a transcription factor binding to a promoter sequence of the eotaxin-1 gene, or inactivation of the eotaxin-1 gene, e.g., through recombinant techniques, etc.

For example, the transcription level of an eotaxin-1 protein can be regulated by gene silencing using RNAi agents, e.g., double-strand RNA (see e.g., Sharp, Genes and Development (1999) 13: 139-141). RNAi, such as double-stranded RNA interference (dsRNAi) or small interfering RNA (siRNA), has been extensively documented in the nematode C. elegans (Fire, et al, Nature (1998) 391:806-811) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in published PCT Application Publication Nos. WO 03/010180 and WO 01/68836, the disclosures of which applications are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al., Biochem. Int. (1987) 14:1015; Bhattacharyya, Nature (1990) 343:484; and U.S. Pat. No. 5,795,715, the disclosures of which are incorporated herein by reference. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. Development (1997)124:1133-1137; and Wianny, et al., Chromosoma (1998) 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct. Specific examples of RNAi agents that may be employed to reduce eotaxin-1 expression include, but are not limited to: MBS8238622 from MyBioSource; CCL11 (Gene ID 6356) Human shRNA available from OriGene (Référence SR304280), CCL11 siRNA/shRNA/RNAi Lentivirus (Human) (Target a) available from ABM; etc.

In some instances, antisense molecules can be used to down-regulate expression of an eotaxin-1 gene in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule.

Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. Short oligonucleotides, of from 7 to 8 bases in length, can be strong and selective inhibitors of gene expression (see Wagner et al., Nature Biotechnol. (1996)14:840-844).

A specific region or regions of the endogenous sense strand mRNA sequence are chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S -phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g., ribozymes, anti-sense conjugates, etc., may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al., Nucl. Acids Res. (1995) 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. Appl. Biochem. Biotechnol. (1995) 54:43-56.

In another embodiment, the eotaxin-1 gene is inactivated so that it no longer expresses a functional protein. By inactivated is meant that the gene, e.g., coding sequence and/or regulatory elements thereof, is genetically modified so that it no longer expresses a functional eotaxin-1 protein, e.g., at least with respect to eotaxin-1 aging impairment activity. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference. Also of interest are CRISPR-CAS mediated gene silencing methods, e.g., as described in Published PCT Application Nos. WO/2015/071474, WO/2014/165825, WO/2015/006498, WO/2014/093595, WO/2015/089427, WO/2014/093694, WO/2015/021426, WO/2015/065964, WO/2015/089462, WO/2015/089486, WO/2014/093661, WO/2015/089419, the disclosures of which are herein incorporated by reference.

Also of interest in certain embodiments are dominant negative mutants of eotaxin-1 proteins, where expression of such mutants in the cell result in a modulation, e.g., decrease, in eotaxin-1 mediated aging impairment. Dominant negative mutants of eotaxin-1 are mutant proteins that exhibit dominant negative eotaxin-1 activity. As used herein, the term "dominant-negative eotaxin-1 activity" or "dominant negative activity" refers to the inhibition, negation, or diminution of certain particular activities of eotaxin-1, and specifically to eotaxin-1 mediated aging impairment. Dominant negative mutations are readily generated for corresponding proteins. These may act by several different mechanisms, including mutations in a substrate-binding domain; mutations in a catalytic domain; mutations in a protein binding domain (e.g., multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz, Nature (1987) 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In some instances, the systemic acid level of eotaxin-1 is reduced by removing systemic eotaxin-1 from the adult mammal, e.g., by removing eotaxin-1 from the circulatory system of the adult mammal. In such instances, any convenient protocol for removing circulatory eotaxin-1 may be employed. For example, blood may be obtained from the adult mammal and extra-corporeally processed to remove eotaxin-1 from the blood to produce eotaxin-1 depleted blood, which resultant eotaxin-1 depleted blood may then be returned to the adult mammal. Such protocols may employ a variety of different techniques in order to remove eotaxin-1 from the obtained blood. For example, the obtained blood may be contacted with a filtering component, e.g., a membrane, etc., which allows passage of eotaxin-1 but inhibits passage of other blood components, e.g., cells, etc. In some instances, the obtained blood may be contacted with an eotaxin-1 absorptive component, e.g., porous bead or particulate composition, which absorbs eotaxin-1 from the blood. In yet other instances, the obtained blood may be contacted with an eotaxin-1 binding member stably associated with a solid support, such that eotaxin-1 binds to the binding member and is thereby immobilized on the solid support, thereby providing for separation of eotaxin-1 from other blood constituents. The protocol employed may or may not be configured to selectively remove eotaxin-1 from the obtained blood, as desired.

In some instances, the eotaxin-1/CCR3 interaction is modulated by reducing active cell surface CCR3 in the mammal. By reducing active cell surface CCR3 is meant lowering the amount or level of CCR3 that is present on cell surfaces and available for binding to eotaxin-1 in a manner that CCR3 is responsive to the presence of eotaxin-1. While the magnitude of the reduction may vary, in some instances the magnitude is 2-fold or greater, such as 5-fold or greater, including 10-fold or greater, e.g., 15-fold or greater, 20-fold or greater, 25-fold or greater (as compared to a suitable control), where in some instances the magnitude is such that the amount of detectable cell surface active CCR3 of the individual is 50% or less, such as 25% or less, including 10% or less, e.g., 1% or less, relative to the amount that was detectable prior to intervention according to the invention, and in some instances the amount is undetectable following intervention.

The active cell surface CCR3 level may be reduced using any convenient protocol. In some embodiments, the active cell surface CCR3 level is reduced by administering to the mammal an effective amount of an active cell surface CCR3 reducing agent, i.e., an agent whose administration results in the reduction of cell surface active CCR3, e.g., CCR3 that can bind to eotaxin-1. As such, in practicing methods according to these embodiments of the invention, an effective amount of the active agent, e.g., CCR3 modulatory agent, is provided to the adult mammal.

Depending on the particular embodiments being practiced, a variety of different types of active agents may be employed. In some instances, the agent is an agent that modulates, e.g., inhibits, CCR3 activity by binding to CCR3 and/or inhibiting binding of CCR3 to a ligand therefore, e.g., eotaxin-1. For example, agents that bind to CCR3 and inhibit its activity are of interest. In certain of these embodiments, the administered active agent is a CCR3 specific binding member. In general, useful CCR3 specific binding members exhibit an affinity (Kd) for a target CCR3, such as human CCR3, that is sufficient to provide for the desired reduction in aging associated impairment CCR3 activity. The term "affinity" and "binding" have the meanings provided above.

Examples of CCR3 specific binding members include CCR3 antibodies and binding fragments thereof. Non-limiting examples of such antibodies include antibodies directed against any epitope of CCR3, e.g., the surface displayed epitope(s) of CCR3. Also encompassed are bispecific antibodies, i.e., antibodies in which each of the two binding domains recognizes a different binding epitope.

Cloning of human CCR3 was reported in Daugherty et al., "Cloning, expression, and characterization of the human eosinophil eotaxin receptor," J. Exp. Med. (1996) 183: 2349-2354. The amino acid sequence of human CCR3 is MTTSLDTVET FGTTSYYDDV GLLCEKADTR ALMAQFVPPL YSLVFTVGLL GNWWMILI KYRRL-RIMTN IYLLNLAISD LLFLVTLPFW IHYVRGHNWV FGHGMCKLLS GFYHTGLYSE IFFIILLTID RYLAIVHAVF ALRARTVTFG VITSIVTWGL AVLAALPEFI FYETEELFEE TLCSALYPED TVYSWRHFHT LRMTIFCLVL PLLVMAICYT GIIK-TLLRCP SKKKYKAIRL IFVIMAVFFI FWTPYNVAIL LSSYQSILFG NDCERSKHLD LVMLVTEVIA YSHCC-MNPVI YAFVGERFRK YLRHFFHRHL LMHLGRYIPF LPSEKLERTS SVSPSTAEPE LSIVF (SEQ ID NO:02). Antibody specific binding members that may be employed include full antibodies or immunoglobulins of any isotype, as well as fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein, e.g., as described above. Specific examples of CCR3 antibodies include, but are not limited to: 12D5 monoclonal antibody (mAb), e.g., as described in Li et al., Acta Trop. (2012) 121:118-24; MaB155 from R& D Systems; as well as those described in U.S. Pat. Nos. 6,207,155; 6,610,834; 8,778,616

CCR3 binding agents that may be employed also include small molecules that bind to the CCR3 and inhibit its activity, i.e., CCR3 small molecule antagonists. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

Specific examples of small molecule agents that bind to CCR3 include, but are not limited to: SB328437 (i.e., (S)-Methyl-2-naphthoylamino-3-(4-nitrophenyl)propionate) which is commercially available, for example from Calbiochem, SB 297006 (i.e., N-Benzoyl-4-nitroaniline ethyl ester; W-56750 (i.e., 4-(3-aminophenyl)thiazol-2-ylthio]-N-[1-(3,4-dichlorobenzyl)piperidin-4-yl]acetamide) which is available commercially from Mitsubishi Tanabe Pharma Co.); GW766944 and GW824575 (GlaxoSmithKline); UCB 35625 (i.e., 1,4-trans-1-(1-Cycloocten-1-ylmethyl)-4-[[(2,7-dichloro-9H-xanthen-9-yl)carbonyl]amino]-1-ethylpiperidinium iodide); piperidine derivatives, piperidine amides and biperidine compounds such as those described in U.S. Pat. Nos. 6,984,651 and 6,903,115, and U.S. published applications 20050176708, 20050182094 and 20050182095 issued as U.S. Pat. No. 7,705,153; heterocyclic piperidines such as those described in U.S. Pat. No. 6,759,411; diphenyl-piperidine derivatives such as those described in U.S. Pat. No. 6,566,376; 2,5-substituted pyrimidine derivatives such as those described in U.S. Pat. No. 6,984,643; piperizinones such as those described in U.S. Pat. No. 6,974,869; cyclic amines such as those described in U.S. Pat. No. 7,576,117; bicycylic and tricyclic amines such as those described in U.S. Pat. No. 6,960,666; N-ureidoalkyl-piperidines such as those described in U.S. Pat. Nos. 6,949,546, 6,919,368, 6,906,066, 6,897,234, 6,875,776, 6,780,857, 6,627,629, 6,521,592 and 6,331,541; bicyclic diamines such as those described in U.S. Pat. No. 6,821,964; benzylcycloalkyl amines such as those described in U.S. Pat. No. 6,864,380; 2-substituted-4-nitrogen heterocycles such as those described in U.S. Pat. No. 6,706,735; ureido derivatives of poly-4-amino-2-carboxy-I-methyl pyrrole compounds; bicyclic and bridged nitrogen heterocycles such as those described in U.S. published application 20050234034; azetidine derivatives such as those described in U.S. published application 20050222118; substituted fused bicyclic amines such as those described in U.S. published application 20050197373; substituted spiro azabicyclics such as those described in U.S. published application 20050197325; piperidine-substituted indoles or heteroderivatives thereof such as those described in U.S. published application 20050153979; piperidinyl and piperazinyl compounds substituted with bicyclo-heterocyclylalkyl groups such as those described in U.S. published application20050090504, arylsulfonamide derivatives such as those described in U.S. published application 20050070582; 1-phenyl-1,2-diaminoethane derivatives such as those described in U.S. published application 20040063779; (N-{[2S]-4-(3,4-dichlorobenzyl)morpholin-2-yl}methyl)-N'[(2-methyl-2H-tetraazol-5-yl)methyl]urea) (see, e.g., Nakamura et al., Immunol Res., 33:213-222, 2006; the CCR3 antagonist compounds described in Suzuki et al., Biochem. Biophys. Res. Commun., 339:1217-1223, 2006; Morokata et al., J. Pharmacol. Exp. Ther., Dec. 9, 2005 [Epub ahead of print]); bipiperidine amide antagonists of CCR3 such as those described in Ting et al., Bioorg. Med. Chem. Lett, 15:3020-3023, 2005; (S)-methyl-2-naphthoylamino-3-(4-nitrophenyl)propionate (see, e.g., Beasley et al., J. Allergy Clin. Immunol., 105: S466-S472, 2000; and the CCR3 antagonist compounds described in Fryer et al., J. Clin. Invest., 1 16:228-236, 2006; as well as those described in Kriegl et al., Bioorganic & Medicinal Chemistry Letters (2015) 25: 229-235. In some instances, the small molecule is not a compound described in U.S. Pat. No. 7,576,117 or 7,705,153.

In some instances, the agent modulates expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of a CCR3 protein. Inhibition of CCR3 protein expression may be accomplished using any convenient means, including use of an agent that inhibits eotaxin-1 protein expression, such as, but not limited to: RNAi agents, antisense agents, agents that interfere with a transcription factor binding to a promoter sequence of the CCR3 gene, or inactivation of the CCR3 gene, e.g., through recombinant techniques, etc. Further details regarding these various types of active agents are provided above.

Also of interest in certain embodiments are dominant negative mutants of CCR proteins, where expression of such mutants in the cell result in a modulation, e.g., decrease, in CCR3 mediated aging impairment. Details regarding dominant negative mutants are further described above.

In those embodiments where an active agent is administered to the adult mammal, the active agent(s) may be administered to the adult mammal using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like.

Preferred dosages for a given compound are readily determinable by those of skill in the art by a variety of means.

In those embodiments where an effective amount of an active agent is administered to the adult mammal, the amount or dosage is effective when administered for a suitable period of time, such as one week or longer, including two weeks or longer, such as 3 weeks or longer, 4 weeks or longer, 8 weeks or longer, etc., so as to evidence a reduction in the impairment, e.g., cognition decline and/or cognitive improvement in the adult mammal. For example, an effective dose is the dose that, when administered for a suitable period of time, such as at least about one week, and maybe about two weeks, or more, up to a period of about 3 weeks, 4 weeks, 8 weeks, or longer, will slow e.g., by about 20% or more, e.g., by 30% or more, by 40% or more, or by 50% or more, in some instances by 60% or more, by 70% or more, by 80% or more, or by 90% or more, e.g., will halt, cognitive decline in a patient suffering from natural aging or an aging-associated disorder. In some instances, an effective amount or dose of active agent will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a period of about 3 weeks, 4 weeks, 8 weeks, or longer will improve the cognitive abilities of an individual suffering from an aging-associated cognitive impairment by, for example 1.5-fold, 2-fold, 3-fold, 4-fold, 5-fold, in some instances 6-fold, 7-fold, 8-fold, 9-fold, or 10-fold or more relative to cognition prior to administration of the blood product.

Where desired, effectiveness of treatment may be assessed using any convenient protocol. Cognition tests and IQ test for measuring cognitive ability, e.g., attention and concentration, the ability to learn complex tasks and concepts, memory, information processing, visuospatial function, the ability to produce and understanding language, the ability to solve problems and make decisions, and the ability to perform executive functions, are well known in the art, any of which may be used to measure the cognitive ability of the individual before and/or during and after treatment with the subject blood product, e.g., to confirm that an effective amount has been administered. These include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, the Alzheimer's Disease Assessment Scale (ADAS-Cog), the Psychogeriatric Assessment Scale (PAS) and the like. Progression of functional brain improvements may be detected by brain imaging techniques, such as Magnetic Resonance Imaging (MRI) or Positron Emission Tomography (PET) and the like. A wide range of additional functional assessments may be applied to monitor activities of daily living, executive functions, mobility, etc. In some embodiments, the method comprises the step of measuring cognitive ability, and detecting a decreased rate of cognitive decline, a stabilization of cognitive ability, and/or an increase in cognitive ability after administration of the blood product as compared to the cognitive ability of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, the reduction in synaptic plasticity and loss of synapses that occurs during the natural aging process or during the progression of an aging-associated disorder. In other words, cells present in adult mammals treated in accordance with methods of the invention will become more responsive to cues, e.g., activity cues, which promote the formation and maintenance of synapses.

Performance of methods of the invention, e.g., as described above, may manifest as improvements in observed synaptic plasticity, both in vitro and in vivo as an induction of long term potentiation. For example, the induction of LTP in neural circuits may be observed in awake individuals, e.g., by performing non-invasive stimulation techniques on awake individuals to induce LTP-like long-lasting changes in localized neural activity (Cooke S F, Bliss T V (2006) Plasticity in the human central nervous system. Brain. 129 (Pt 7):1659-73); mapping plasticity and increased neural circuit activity in individuals, e.g., by using positron emission tomography, functional magnetic resonance imaging, and/or transcranial magnetic stimulation (Cramer and Bastings, "Mapping clinically relevant plasticity after stroke," Neuropharmacology (2000)39:842-51); and by detecting neural plasticity following learning, i.e., improvements in memory, e.g., by assaying retrieval-related brain activity (Buchmann et al., "Prion protein M129V polymorphism affects retrieval-related brain activity," Neuropsychologia. (2008) 46:2389-402) or, e.g., by imaging brain tissue by functional magnetic resonance imaging (fMRI) following repetition priming with familiar and unfamiliar objects (Soldan et al., "Global familiarity of visual stimuli affects repetition-related neural plasticity but not repetition priming," Neuroimage. (2008) 39:515-26; Soldan et al., "Aging does not affect brain patterns of repetition effects associated with perceptual priming of novel objects," J. Cogn. Neurosci. (2008) 20:1762-76). In some embodiments, the method includes the step of measuring synaptic plasticity, and detecting a decreased rate of loss of synaptic plasticity, a stabilization of synaptic plasticity, and/or an increase in synaptic plasticity after administration of the blood product as compared to the synaptic plasticity of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

In some instances, the methods result in a change in expression levels of one or more genes in one or more tissues of the host, e.g., as compared to a suitable control (such as described in the Experimental section, below). The change in expression level of a given gene may be 0.5 fold or greater, such as 1.0 fold or greater, including 1.5 fold or greater. The tissue may vary, and in some instances is nervous system tissue, e.g., central nervous system tissue, including brain tissue, e.g., hippocampal tissue. In some instances, the modulation of hippocampal gene expression is manifested as enhanced hippocampal plasticity, e.g., as compared to a suitable control.

In some instances, treatment results in an enhancement in the levels of one or more proteins in one or more tissues of the host, e.g., as compared to a suitable control (such as described in the Experimental section, below). The change in protein level of a given protein may be 0.5 fold or greater, such as 1.0 fold or greater, including 1.5 fold or greater, where in some instances the level may approach that of a healthy wild-type level, e.g., within 50% or less, such as 25% or less, including 10% or less, e.g., 5% or less of the healthy wild-type level. The tissue may vary, and in some instances is nervous system tissue, e.g., central nervous system tissue, including brain tissue, e.g., hippocampal tissue.

In some instances, the methods result in one or more structural changes in one or more tissues. The tissue may vary, and in some instances is nervous system tissue, e.g., central nervous system tissue, including brain tissue, e.g., hippocampal tissue. Structure changes of interest include an increase in dendritic spine density of mature neurons in the dentate gyrus (DG) of the hippocampus, e.g., as compared to a suitable control. In some instances, the modulation of hippocampal structure is manifested as enhanced synapse formation, e.g., as compared to a suitable control. In some instances, the methods may result in an enhancement of long term potentiation, e.g., as compared to a suitable control.

In some instances, practice of the methods, e.g., as described above, results in an increase in neurogenesis in the adult mammal. The increase may be identified in a number of different ways, e.g., as described below in the Experimental section. In some instances, the increase in neurogenesis manifests as an increase the amount of Dcx-positive immature neurons, e.g., where the increase may be 2-fold or greater. In some instances, the increase in neurogenesis manifests as an increase in the number of BrdU/NeuN positive cells, where the increase may be 2-fold or greater.

In some instances, the methods result in enhancement in learning and memory, e.g., as compared to a suitable control. Enhancement in learning and memory may be evaluated in a number of different ways, e.g., the contextual fear conditioning and/or radial arm water maze (RAWM) paradigms described in the experimental section, below. When measured by contextual fear conditioning, treatment results in some instances in increased freezing in contextual, but not cued, memory testing. When measured by RAWM, treatment results in some instances in enhanced learning and memory for platform location during the testing phase of the task. In some instances, treatment is manifested as enhanced cognitive improvement in hippocampal-dependent learning and memory, e.g., as compared to a suitable control.

In some embodiments, eotaxin-1/CCR3 interaction modulation, e.g., as described above, may be performed in conjunction with an active agent having activity suitable to treat aging-associated cognitive impairment. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some aspects of the subject methods, the method further comprises the step of measuring cognition and/or synaptic plasticity after treatment, e.g., using the methods described herein or known in the art, and determining that the rate of cognitive decline or loss of synaptic plasticity have been reduced and/or that cognitive ability or synaptic plasticity have improved in the individual. In some such instances, the determination is made by comparing the results of the cognition or synaptic plasticity test to the results of the test performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a cognitive impairment, e.g., using the methods described herein or known in the art for measuring cognition and synaptic plasticity, prior to administering the subject plasma-comprising blood product. In some instances, the diagnosing will comprise measuring cognition and/or synaptic plasticity and comparing the results of the cognition or synaptic plasticity test to one or more references, e.g., a positive control and/or a negative control. For example, the reference may be the results of the test performed by one or more age-matched individuals that experience aging-associated cognitive impairments (i.e., positive controls) or that do not experience aging-associated cognitive impairments (i.e., negative controls). As another example, the reference may be the results of the test performed by the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having an aging-associated disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

Utility

The subject methods find use in treating, including preventing, aging-associated impairments and conditions associated therewith, such as impairments in the cognitive ability of individuals. Individuals suffering from or at risk of developing an aging-associated cognitive impairments include individuals that are about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.), and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's Disease (AD). Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease. Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function. In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal Dementia. Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's Disease. Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic Lateral Sclerosis. Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis. Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma. Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012;21(4):250-254).

Macular degeneration. Macular degeneration is a clinical term that is used to describe a family of diseases that are all characterized by a progressive loss of central vision associated with abnormalities of Bruch's membrane, the choroid, the neural retina and/or the retinal pigment epithelium. These disorders include very common conditions that affect older subjects—such as Age-related macular degeneration (AMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease and Malattia leventinese.

AMD is the leading cause of permanent vision loss for individuals over age 65, currently affecting approximately 15 million Americans. AMD affects light-sensitive photoreceptor cells and pigmented epithelial cells in the macula, the center of the retina of the eye. While it may not cause total blindness, the disease destroys central vision, making reading, watching electronic monitor screens and driving impossible. It has no documented cure, has never demonstrated spontaneous remission and effective treatments are very limited.

The retina is a complicated network of nerve cells that changes light into nerve impulses that travel to the brain where they are interpreted as visual images. The central part of the retina, called the macula, is responsible for vision that is needed for reading and other detailed work. Damage to the macula results in poor vision. The most common disease process that affects the macula is AMD. In patients with AMD, retinal photoreceptor and pigment epithelial cells in the macula die over the course of several years. The cell death and gradual visual loss usually do not begin until age 60 or older, hence the name age-related macular degeneration.

There are two types of AMD: dry macular degeneration and wet macular degeneration. Dry macular degeneration, although more common, typically results in a less severe, more gradual loss of vision. Patients who are affected by dry AMD have gradual loss of central vision due to the death of photoreceptor cells and their close associates, retinal pigmented epithelial (RPE) cells, with deposition of a complex waxy amyloid mixture, termed 'drusen'. Photoreceptors, the cells in the retina that actually 'see' light, are essential for vision. Macrophagic RPE cells are necessary for photoreceptor survival, function and renewal. Patients with wet macular degeneration develop new blood vessels under the retina. As the photoreceptor and RPE cells slowly degenerate, there is a tendency for blood vessels to grow from their normal location in the choroid into an abnormal location beneath the retina. This abnormal new blood vessel growth is called choroidal neovascularization (CNV). The abnormal blood vessels leak and bleed, causing hemorrhage, swelling, scar tissue, and severe loss of central vision. Only 10% of patients with AMD have the wet type, but it is responsible for 90% of all blindness resulting from AMD.

Myotonic dystrophy. Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia. Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed.

Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Progressive supranuclear palsy. Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-system atrophy. Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

The subject methods and compositions also find use in reducing cognitive impairment in an individual suffering from cognitive decline as a consequence of systemic inflammation, radiation, chemotherapy, frailty, and kidney dysfunction. The subject methods and compositions also find use in reducing, if not preventing, age-associated brain inflammation, neurodegeneration and cognitive decline.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of modulating eotaxin-1/CCR3 interaction in an adult mammal.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

The following examples are provided by way of illustration and not by way of limitation.

EXPERIMENTAL

I. Materials and Methods
A. Summary of Methods

C57BL/6 (Jackson Laboratory), C57BL/6 aged mice (National Institutes of Aging), Dcx-Luc26, and C57BL/6J-Act-GFP (Jackson Laboratory). For all in vivo pharmacological and behavioral studies young (2-3 months) wild type C57BL/6 male mice were used. All animal use was in accordance with institutional guidelines approved by the VA Palo Alto Committee on Animal Research. Parabiosis surgery followed previously described procedures (Monje et al., Science (2003) 302: 1760-1765) with the addition that peritonea between animals were surgically connected. Immunohistochemistry was performed on free-floating sections following standard published techniques (Luo et al., J Clin Invest (2007) 117: 3306-3315). Hippocampal slice extracellular electrophysiology was performed as previously described (Xie & Smart, Pflugers Arch (1994) 427: 481-486). Spatial learning and memory was assayed with the radial arm water maze (RAWM) paradigm as previously published (Alamed et al., Nat Protoc (2006)1:1671-1679). Mouse plasma was prepared by centrifugation and systemically administered via intravenous injections. Relative plasma concentrations of cytokines and signaling molecules in mice and humans were measured using antibody-based multiplex immunoassays at Rules Based Medicine, Inc. Human plasma and CSF samples were obtained from academic centers and informed consent was obtained from human subjects according to the institutional review board guidelines at the respective centers. Recombinant murine CCL11 (R&D Systems), rat IgG2a neutralizing antibody against mouse CCL11 (R&D Systems), and control rat IgG2a (R&D Systems) were administered either systemically by intraperitoneal injection or locally by unilateral stereotaxic injection into the dentate gyrus of the hippocampus. Statistical analysis was performed with Prism 5.0 software (GraphPad Software). Plasma protein correlations in the aging samples were analyzed with the Significance Analysis of Microarray software (SAM 3.00 algorithm).

B. Mice

The following mouse lines were used: C57BL/6 (The Jackson Laboratory), C57BL/6 aged mice (National Institutes of Aging), Dcx-Luc mice (Couillard-Despres et al., Mol Imaging (2008) 7:28-34), and C57BL/6J-Act-GFP (Jackson Laboratory). For all in vivo pharmacological and behavioral studies young (2-3 months) wild type C57BL/6 male mice were used. Mice were housed under specific pathogen-free conditions under a 12 h light-dark cycle and all animal handling and use was in accordance with institutional guidelines approved by the VA Palo Alto Committee on Animal Research. All experiments were done in a randomized and blinded fashion.

C. Immunohistochemistry

Tissue processing and immunohistochemistry was performed on free-floating sections following standard published techniques (Luo et al., J Clin Invest (2007) 117:3306-3315). Briefly, mice were anesthetized with 400 mg/kg chloral hydrate (Sigma-Aldrich) and transcardially perfused with 0.9% saline Brains were removed and fixed in phosphate-buffered 4% paraformaldehyde, pH 7.4, at 4° C. for 48 h before they were sunk through 30% sucrose for cryoprotection. Brains were then sectioned coronally at 40 μm with a cryomicrotome (Leica Camera, Inc.) and stored in cryoprotective medium. Primary antibodies were: goat anti-Dcx (1:500; Santa Cruz Biotechnology), rat anti-BrdU (1:5000, Accurate Chemical and Scientific Corp.), goat anti-Sox2 (1:200; Santa Cruz), mouse anti-NeuN (1:1000, Chemicon), mouse anti-GFAP (1:1500, DAKO), and mouse anti-CD68 (1:50, Serotec). After overnight incubation, primary antibody staining was revealed using biotinylated secondary antibodies and the ABC kit (Vector) with Diaminobenzidine (DAB, Sigma-Aldrich) or fluorescence conjugated secondary antibodies. For BrdU labeling, brain sections were pre-treated with 2N HCl at 37° C. for 30 min before incubation with primary antibody. For double-label immunofluorescence of BrdU/NeuN or BrdU/GFAP, sections were incubated overnight with rat anti-BrdU, rinsed, and incubated for 1 hr with donkey anti-rat antibody (2.5 μg/ml, Vector) before they were stained with mouse anti-NeuN antibody.

To estimate the total number of Dcx or Sox2 positive cells per DG immunopositive cells in the granule cell and subgranular cell layer of the DG were counted in every sixth coronal hemibrain section through the hippocampus and multiplied by 12.

D. BrdU Administration and Quantification of BrdU-Positive Cells 50 mg/kg of BrdU was injected intraperitoneally into mice once a day for 6 days, and mice were sacrificed 28 days later or injected daily for 3 days before sacrifice. To estimate the total number of BrdU-positive cells in the brain, we performed DAB staining for BrdU on every sixth hemibrain section. The number of BrdU+ cells in the granule cell and subgranular cell layer of the DG were counted and multiplied by 12 to estimate the total number of BrdU-positive cells in the entire DG. To determine the fate of dividing cells a total of 200 BrdU-positive cells across 4-6 sections per mouse were analyzed by confocal microscopy for co-expression with NeuN and GFAP. The number of double-positive cells was expressed as a percentage of BrdU-positive cells.

E. Parabiosis and Flow Cytometry

Parabiosis surgery followed previously described procedures (Conboy et al., Nature (2005) 433: 760-764). Pairs of mice were anesthetized and prepared for surgery. Mirror-image incisions at the left and right flanks, respectively, were made through the skin. Shorter incisions were made through the abdominal wall. The peritoneal openings of the adjacent parabionts were sutured together. Elbow and knee joints from each parabiont were sutured together and the skin of each mouse was stapled (9 mm Autoclip, Clay Adams) to the skin of the adjacent parabiont. Each mouse was injected subcutaneously with Baytril antibiotic and Buprenex as directed for pain and monitored during recovery. Flow cytometric analysis was done on fixed and permeabilized blood plasma cells from GFP and non-GFP parabionts. Approximately 40-60% of cells in the blood of either parabiont were GFP-positive two weeks after parabiosis surgery. We observed 70-80% survival rate in parabionts five weeks post parabiosis surgery.

F. Extracellular Electrophysiology

Acute hippocampal slices (400 µm thick) were prepared from unpaired and young parabionts. Slices were maintained in artificial cerebrospinal fluid (ACSF) continuously oxygenated with 5% $CO_2$/95% $O_2$. ACSF composition was as follows: (in mM): NaCl 124.0; KCl 2.5; $KH_2PO_4$ 1.2; $CaCl_2$ 2.4; $MgSO_4$ 1.3; $NaHCO_3$ 26.0; glucose 10.0 (pH 7.4). Recordings were performed with an Axopatch-2B amplifier and pClamp 10.2 software (Axon Instruments). Submerged slices were continuously perfused with oxygenated ACSF at a flow rate of 2 ml/min from a reservoir by gravity feeding. Field potential (population spikes and EPSP) was recorded using glass microelectrodes filled with ACSF (resistance: 4-8 M.OMEGA.). Biphasic current pulses (0.2 ms duration for one phase, 0.4 ms in total) were delivered in 10 s intervals through a concentric bipolar stimulating electrode (FHC, Inc.). No obvious synaptic depression or facilitation was observed with this frequency stimulation. To record field population spikes in the dentate gyrus, the recording electrode was placed in the lateral or medial side of the dorsal part of the dentate gyrus. The stimulating electrode was placed right above the hippocampal fissure to stimulate the perforant pathway fibers. Signals were filtered at 1 KHz and digitized at 10 KHz. Tetanic stimulation consisted of 2 trains of 100 pulses (0.4 ms pulse duration, 100 Hz) delivered with an inter-train interval of 5 seconds. The amplitude of population spike was measured from the initial phase of the negative wave. Up to five consecutive traces were averaged for each measurement. LTP was calculated as mean percentage change in the amplitude of the population spike following high frequency stimulation relative to its basal amplitude.

G. Behavioral Assay

Spatial learning and memory was assessed using the radial arm water maze (RAWM) paradigm following the exact protocol described by Alamed et al. Nat Protoc (2006) 1:1671-1679). Behavioral analysis was performed for normal aging mice at young (2-3 months) and old (18 months) ages, for young adult mice (2-3 months) injected intravenously with plasma isolated from young (3-4 months) and old (18-20 months) mice every three days for 24 days, and for young adult mice (3-4 months) injected intraperitoneally with murine recombinant CCL11 and PBS vehicle for five weeks. The goal arm location containing a platform remains constant throughout the training and testing phase, while the start arm is changed during each trial. On day one during the training phase, mice are trained for 15 trails, with trials alternating between a visible and hidden platform. On day two during the testing phase, mice are tested for 15 trials with a hidden platform. Entry into an incorrect arm is scored as an error, and errors are averaged over training blocks (three consecutive trials). All studies were done by an investigator that was blinded to the age or treatment of mice.

H. Plasma Collection and Proteomic Analysis

Mouse blood was collected into EDTA coated tubes via tail vein bleed, mandibular vein bleed, or intracardial bleed at time of sacrifice. EDTA plasma was generated by centrifugation of freshly collected blood and aliquots were stored at –80° C. until use. Human plasma and CSF samples were obtained from academic centers and subjects were chosen based on standardized inclusion and exclusion criteria as previously described (Zhang et al., Am J Clin Pathol (2008)129: 526-529; Li et al., PLoS One 4 (2009) (5), e5424) and outlined below. Mouse and human plasma samples were sent to Rules Based Medicine Inc., a fee-for-service provider, where the relative plasma concentrations of cytokines and signaling molecules were measured using standard antibody-based multiplex immunoassays in a blinded fashion. All assays were developed and validated to Clinical Laboratory Standards Institute (formerly NCCLS) guidelines based upon the principles of immunoassay as described by the manufacturers.

I. CCL11, MSCF, Antibody, or Plasma Administration

Carrier free recombinant murine CCL11 dissolved in PBS (10 µg/kg; R&D Systems), carrier free recombinant MCSF dissolved in PBS (10 µg/kg; Biogen), rat IgG2a neutralizing antibody against mouse CCL11 (50 µg/ml, R&D Systems, Clone: 42285), and isotype matched control rat IgG2a recommended by the manufacturer (R&D Systems, Clone: 54447) were administered systemically via intraperitoneal injection over ten days on day 1, 4, 7, and 10. The same reagents (0.50 µl, 0.1 µg/µl) were also administered stereotaxically into the DG of the hippocampus in some experiments (coordinates from bregma: A=–2.0 mm and L=–1.8 mm, from brain surface: H=–2.0 mm). Pooled mouse serum or plasma was collected from 2-3-month-old (young) mice and 18-20-month-old (aged) mice by intracardial bleed at time of sacrifice. Serum was prepared from clotted blood collected without anticoagulants; plasma was prepared from blood collected with EDTA followed by centrifugation. Aliquots were stored at –80° C. until use. Prior to administration plasma was dialyzed in PBS to remove EDTA. Young adult mice were systemically treated with plasma (100 µl) isolated from young or aged mice via intravenous injections every three days for ten days.

J. In Vivo Bioluminescence Imaging

Bioluminescence was detected with the In Vivo Imaging System (IVIS Spectrum; Caliper Life Science). Mice were injected intraperitoneally with 150 mg/kg D-luciferin (Xenogen) 10 minutes before imaging and anesthetized with isofluorane during imaging. Photons emitted from living mice were acquired as photons/s/cm2/steridan (sr) using LIVINGIMAGE software (version 3.5, Caliper) and integrated over 5 minutes. For quantification a region of interest was manually selected and kept constant for all experiments.

K. Cell Culture Assays

Mouse neural progenitor cells were isolated from C57BL/6 mice as previously described (Renault et al., Cell Stem Cell (2009) 5: 527-539). Brains from postnatal animals (1 day-old) were dissected to remove olfactory bulbs, cerebellum and brainstem. After removing superficial blood vessels forebrains were finely minced, digested for 30 minutes at 37° C. in DMEM media containing 2.5 U/ml Papain (Worthington Biochemicals), 1 U/ml Dispase II (Boeringher Mannheim), and 250 U/ml DNase I (Worthington Biochemicals) and mechanically dissociated. NSC/progenitors were purified using a 65% Percoll gradient and plated on uncoated tissue culture dishes at a density of 105 cells/cm$_2$. NPCs were cultured under standard conditions in NeuroBasal A medium supplemented with penicillin (100 U/ml), streptomycin (100 mg/ml), 2 mM L-glutamine, serum-free B27 supplement without vitamin A (Sigma-Aldrich), bFGF (20 ng/ml) and EGF (20 ng/ml). Carrier free forms of murine recombinant CCL2 (100 ng/ml; R&D Systemcs), murine recombinant CCL11 (100 ng/ml, R&D Systemcs), rat IgG2b neutralizing antibody against mouse CCL2 (10 µg/ml; R&D Systems, Clone: 123616), control rat IgG2b (10 µg/ml, R&D Systems, Clone: 141945), goat IgG neutralizing antibody against mouse CCL11 (10 µg/ml, R&D Systems), and control goat IgG (10 µg/ml, R&D Systems) were dissolved in PBS and added to cell cultures under self-renewal conditions every other day following cell plating.

Human NTERA cells (Renault et al., Cell Stem Cell (2009) 5: 527-539) expressing eGFP under the doublecortin promoter were cultured under standard self-renewal and differentiation conditions (Couillard-Despres et al., BMC Neurosci (2008) 9: 31; Buckwalter et al., Am J Pathol (2006) 169: 154-164). Carrier free forms of human recombinant CCL2 (100 ng/ml, R&D Systems), human recombinant CCL11 (100 ng/ml, R&D Systems), mouse IgG1 neutralizing antibody against human CCL11 (25 µg/ml, R&D Systems, Clone: 43911) and control mouse IgG1 (25 µg/ml, R&D Systems) were added to cell cultures under differentiation conditions every other day following cell plating.

L. Data and Statistical Analysis

Data are expressed as mean±SEM. Statistical analysis was performed with Prism 5.0 software (GraphPad Software). Means between two groups were compared with two-tailed, unpaired Student's t test. Comparisons of means from multiple groups with each other or against one control group were analyzed with 1-way ANOVA and Tukey-Kramer's or Dunnett's post hoc tests, respectively. Plasma protein correlations in the aging samples were analyzed with the Significance Analysis of Microarray software (SAM 3.00 algorithm, see, e.g., R. Hughey and A. Krogh, Technical Report UCSC-CRL-95-7, University of California, Santa Cruz, Calif., January 1995. (Last update prior to filing of application No. 61/298,998), The SAM documentation.). Unsupervised cluster analysis was performed using Gene Cluster 3.0 software and node maps were produced using Java TreeView 1.0.13 software.

II. Results and Discussion

During aging both regenerative capacity and cognitive function dramatically deteriorate in the adult brain (Rando, T. A., Nature (2006) 441:1080-1086; Rapp & Heindel, Curr Opin Neurol (1994) 7: 294-298). Interestingly, associated stem cell and cognitive impairments can be ameliorated through systemic perturbations such as exercise (van Praag et al., J Neurosci (2005) 25: 8680-8685). Here, using heterochronic parabiosis we show that blood-borne factors present in the systemic milieu can inhibit or rejuvenate adult neurogenesis in an age dependent fashion in mice. Accordingly, exposing a young animal to an old systemic environment, or to plasma from old mice, decreased synaptic plasticity and impaired spatial learning and memory. We identify chemokines—including CCL2/MCP-1 and CCL11/Eotaxin—whose plasma levels correlate with reduced neurogenesis in aged mice, and whose levels are increased in plasma and cerebral spinal fluid of healthy aging humans. Finally, increasing peripheral chemokine levels in vivo in young mice decreased adult neurogenesis and impaired spatial learning and memory. Together our data indicate that the decline in neurogenesis, and cognitive impairments, observed during aging can be in part attributed to changes in blood-borne factors.

Stem cell activity decreases dramatically with age in tissues including the brain (Rando, T. A., Nature (2006) 441: 1080-1086). In the central nervous system (CNS), aging results in a decline in adult neural stem/progenitor cells (NPCs) and neurogenesis, with concomitant impairments in cognitive functions (van Praag et al., J Neurosci (2005) 25:8680-8685; Clelland et al., Science (2009) 325: 210-213). Adult neurogenesis occurs in local microenvironments, or neurogenic niches, in the subventricular zone (SVZ) of the lateral ventricles and the subgranular zone (SGZ) of the hippocampus (Gage, F. H., Science (2000) 287:1433-1438; Alvarez-Buylla & Lim, Neuron (2004) 41: 683-686). Permissive cues within the neurogenic niche are thought to drive the production of new neurons and their subsequent integration into the neurocircuitry of the brain (Zhao et al., Cell (2008) 132: 645-660; van Praag et al., Nature (2002) 415: 1030-1034), which directly contributes to cognitive processes including learning and memory (Clelland et al., Science (2009) 325: 210-213; Deng et al., Nat Rev Neurosci (2010) 11:339-350; Zhang et al., Nature (2008) 451: 1004-1007). Importantly, the neurogenic niche is localized around blood vessels (Shen et al., Science (2004) 304: 1338-1340; Carpentier & Palmer, Neuron (2009) 64: 79-92) that lack a classical blood-brain-barrier (BBB) (Shen et al., Cell Stem Cell (2008) 3: 289-300; Tavazoie et al., Cell Stem Cell (2008) 3:279-288; Currie & Gilbertson Cell Stem Cell (2008) 3: 234-236, allowing for potential communication with the systemic environment. Therefore, the possibility arises that diminished adult neurogenesis during aging may be modulated by the balance of two independent forces—intrinsic CNS-derived cues previously reported (Renault et al., Cell Stem Cell (2009) 5: 527-539; Molofsky et al., Nature (2006) 443: 448-452; Lie et al., Nature (2005) 437: 1370-1375), and cues extrinsic to the CNS delivered by blood. We hypothesized that age-related systemic molecular changes could cause a decline in neurogenesis and impair cognitive function during aging.

Figure 6A:
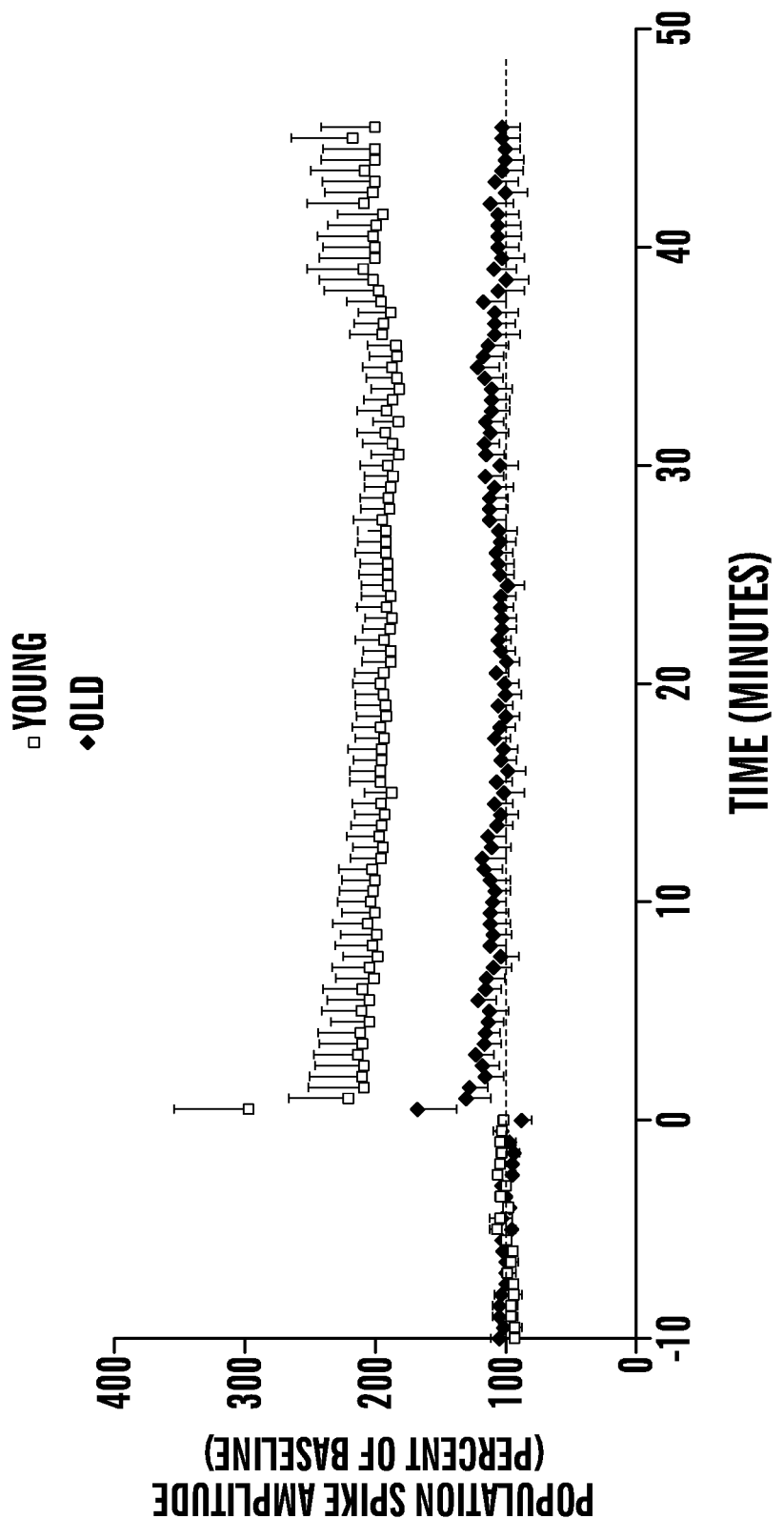
FIGS. 6A-6B show that synaptic plasticity and cognitive function are impaired in the hippocampus of old versus young animals.
Figure 6B:
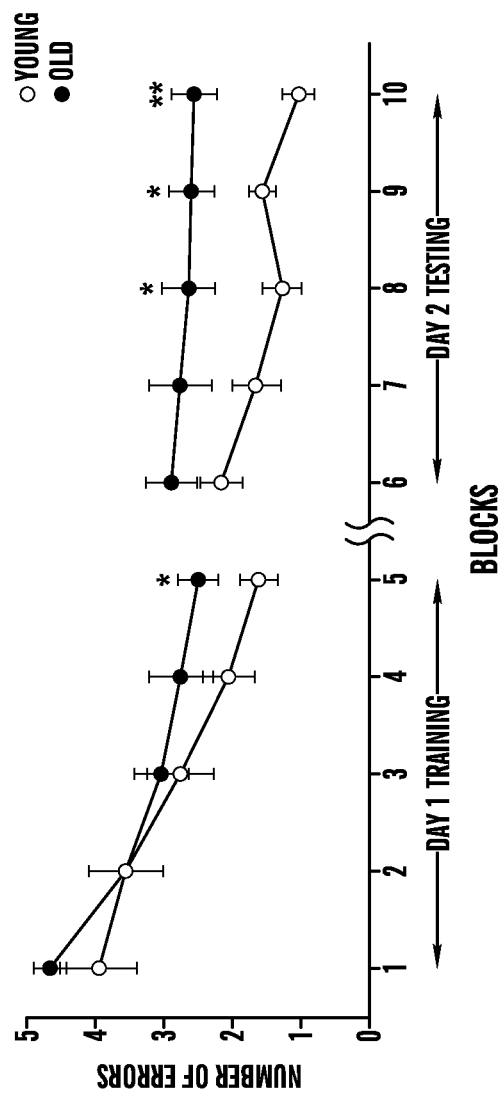

We first characterized the aging neurogenic niche by assessing cellular changes in newly differentiated neurons, neural progenitors, microglia, and astrocytes in the dentate gyrus (DG) of the hippocampus in mice at 6, 12, 18 and 24 months of age (FIG. 5A-5D), and observed changes consistent with a dramatic decrease in adult neurogenesis (van Praag et al., J Neurosci (2005) 25: 8680-8685) and a concomitant increase in neuroinflammation with age (Lucin & Wyss-Coray, Neuron (2009) 64: 110-122). Additionally, we used a long-term potentiation (LTP) paradigm to examine synaptic plasticity, and detected lower LTP levels from the DG of old (18 months) versus young (3 months) animals (FIG. 6A). Lastly, we assessed hippocampal dependent spatial learning and memory using the radial arm water maze (RAWM) paradigm (Alamed et al., Nat Protoc (2006) 1:1671-1679). During the training phase all animals showed learning capacity for the task (FIG. 6B). However, old mice demonstrated impaired learning and memory for platform location compared to young mice during the testing phase of the task (FIG. 6B), consistent with a decrease in cognitive function during normal aging (Rapp & Heindel, Curr Opin Neurol (1994) 7:294-298).

Figure 1B:
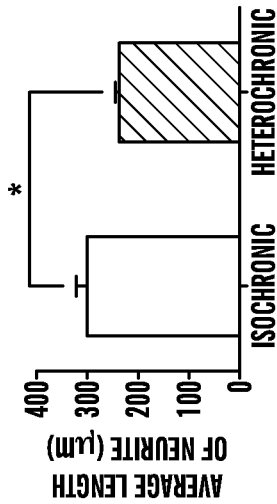
Figure 1C:
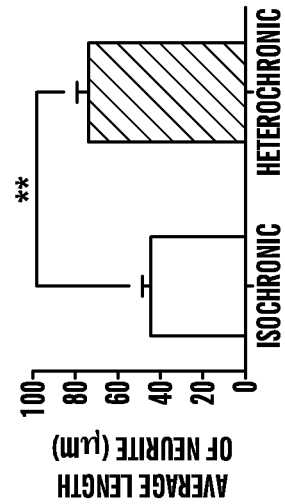
Figure 7A:
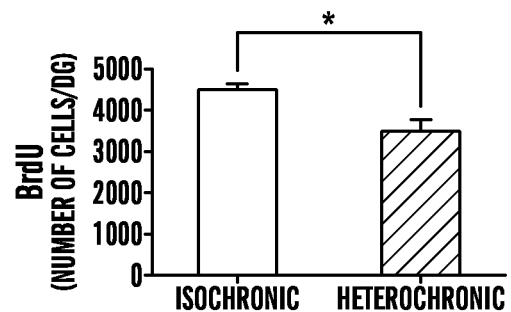
FIGS. 7A-7F show that heterochronic parabiosis reduces proliferation and progenitor frequency in the DG of young animals while increasing proliferation in aged animals. After five weeks of parabiosis, animals were injected with BrdU for three days prior to sacrifice. BrdU immunostaining was performed for young (3-4 months) and aged (18-20 months) isochronic and heterochronic parabionts.
Figure 7B:
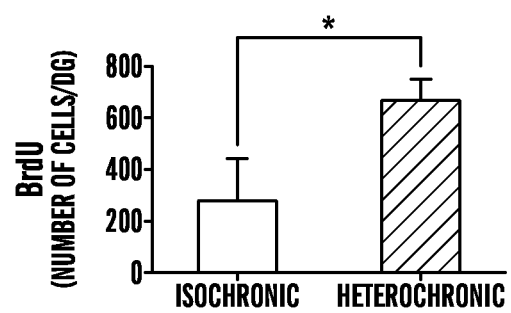
Figure 7C:
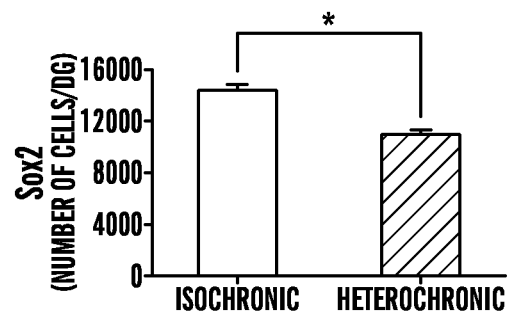
Figure 7D:
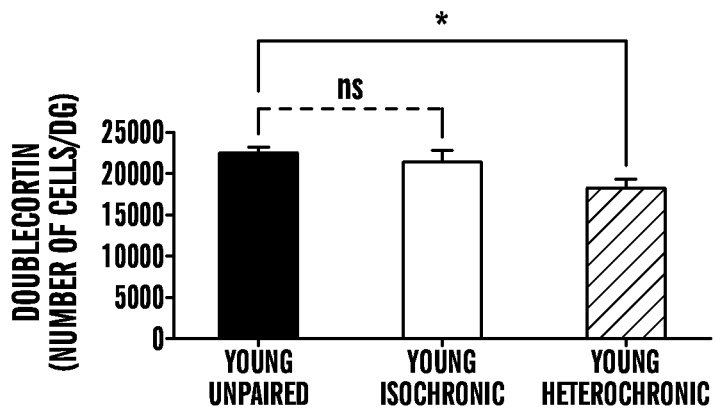
Figure 7E:
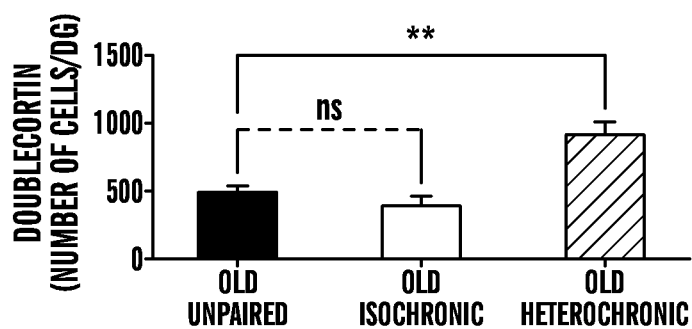

To determine whether peripheral systemic factors contributed to the decline in neurogenesis with age we utilized a model of parabiosis. Specifically, neurogenesis in the DG of the hippocampus was investigated in the setting of isochronic (young-young (3-4 months) and old-old (18-20 months)) and heterochronic (young-old) parabiotic pairings (FIG. 1A). Remarkably, the number of Doublecortin (Dcx)-positive newly born neurons in young heterochronic parabionts decreased 20% compared to young isochronic parabionts (FIG. 1B). Likewise, BrdU-positive cells (FIG. 7B) and Sox2-positive progenitors (FIG. 7C) showed a similar decrease. In contrast, we observed a 3-fold increase in the number of Dcx-positive neurons (FIG. 1C) and BrdU-positive cells (FIG. 7C) in the old heterochronic parabionts compared to isochronic old parabionts. The number of Dcx-positive neurons between unpaired age-matched animals and isochronic animals showed no significant difference, indicating that the parabiosis procedure in it of itself did not account for the observed changes (FIGS. 7D and 7E).

Figure 1D:
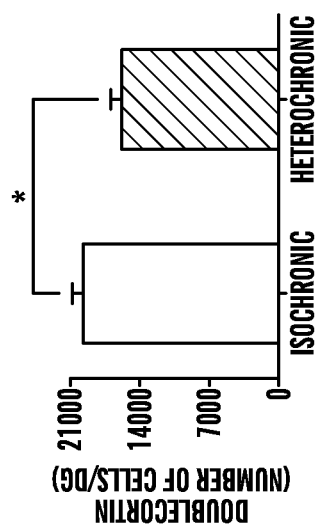
Figure 1E:
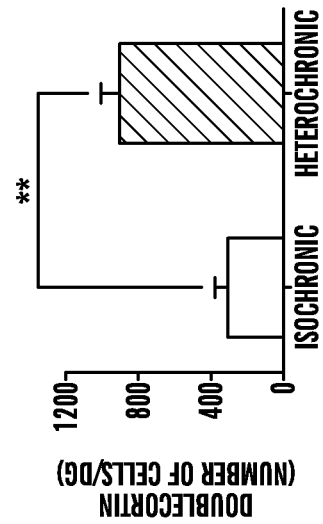
Figure 7F:
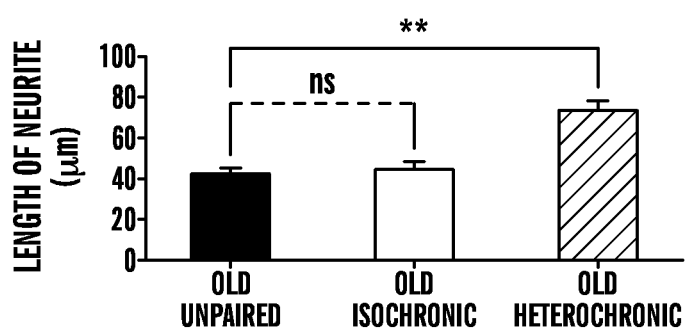
Figure 8B:
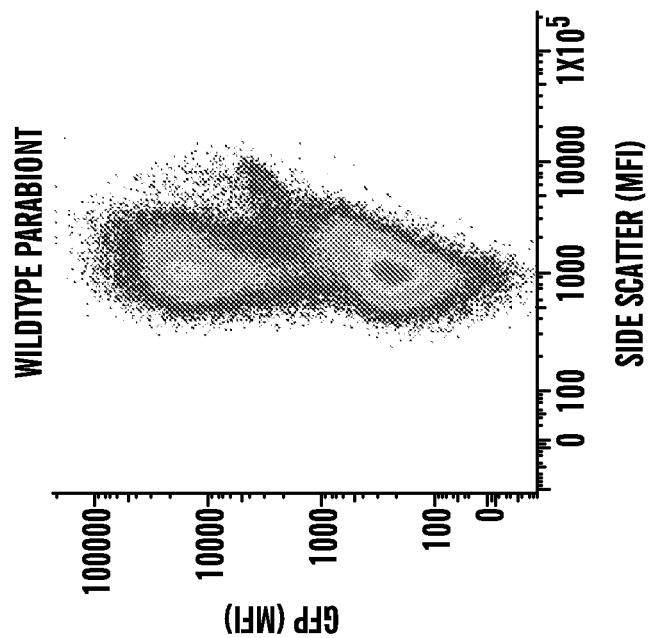
Figure 8A:
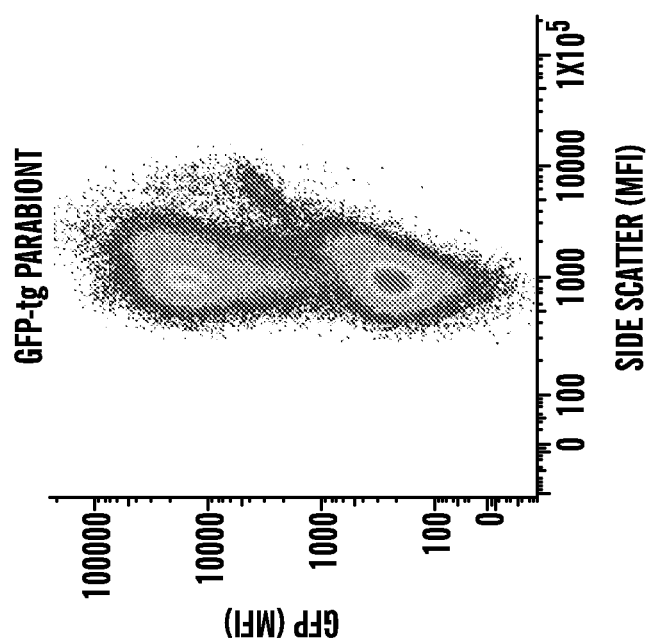

We also compared the neurite length of newly differentiated neurons in isochronic and heterochronic parabionts (FIG. 1D, 1E). Young heterochronic parabionts showed a 20% decrease in length compared to isochronic parabionts (FIG. 1D), while old heterochronic parabionts demonstrated a 40% increase in length compared to age-matched isochronic controls (FIG. 1E). Neurite length between unpaired age-matched animals and isochronic parabionts showed no significant difference (FIG. 7F). As a control, flow cytometry analysis confirmed a shared vasculature in a subset of parabiotic pairs, in which one parabiont was transgenic for green fluorescent protein (GFP, FIG. 8A-8D). Together our findings indicate that global age-dependent systemic changes can modulate neurogenesis and neurite morphology in both the young and aged neurogenic niche, potentially contributing to the decline in regenerative capacity observed in the normal aging brain.

Figure 2A:
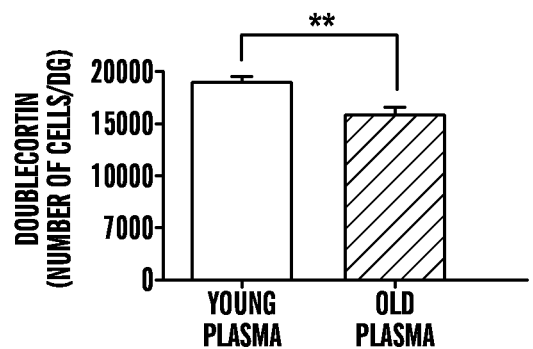
FIGS. 2A-2E show that exposure of a young adult brain to an old systemic environment decreases synaptic plasticity and impairs spatial learning and memory.
Figure 2B:
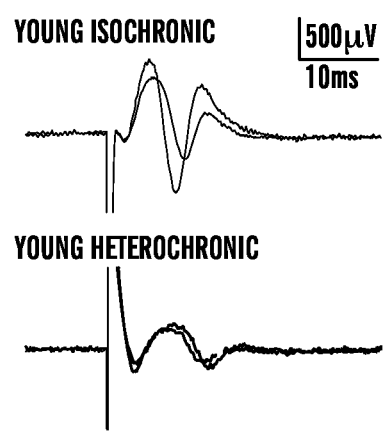
Figure 2C:
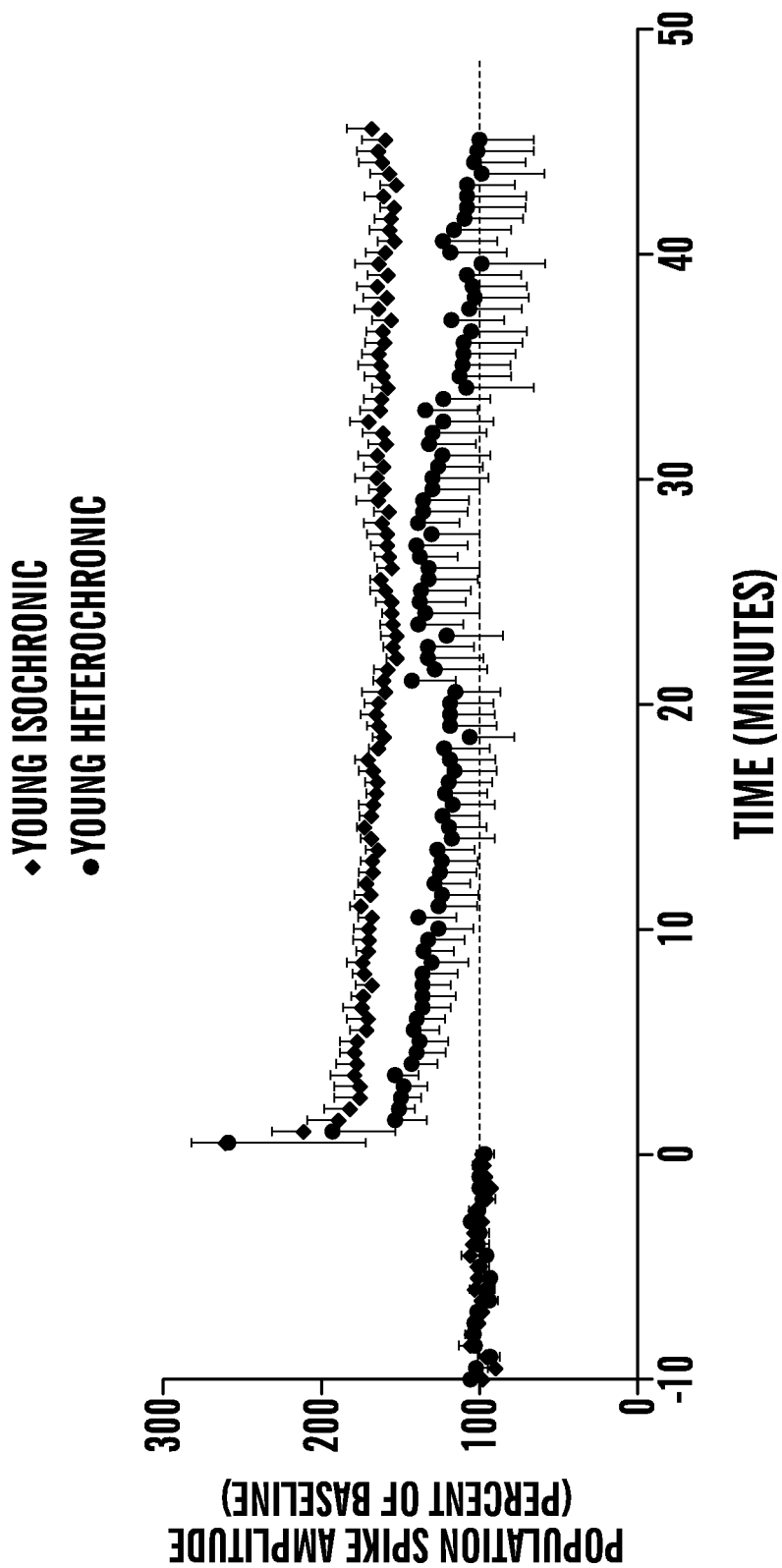
Figure 2D:
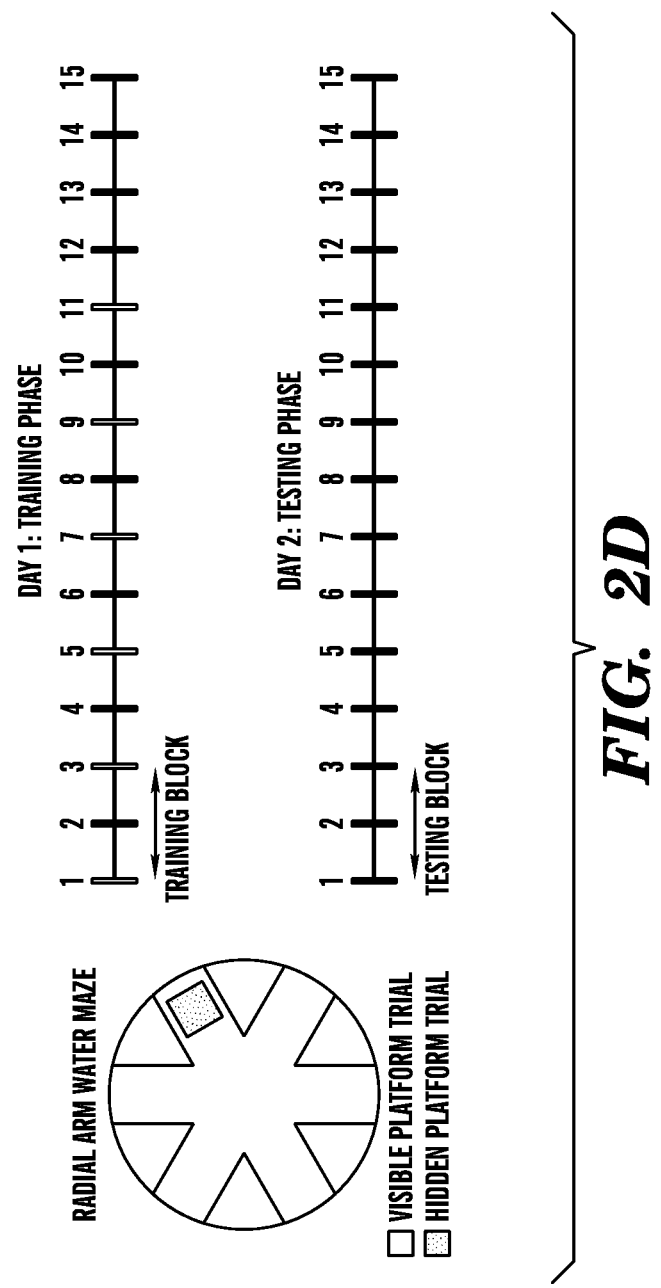
Figure 2E:
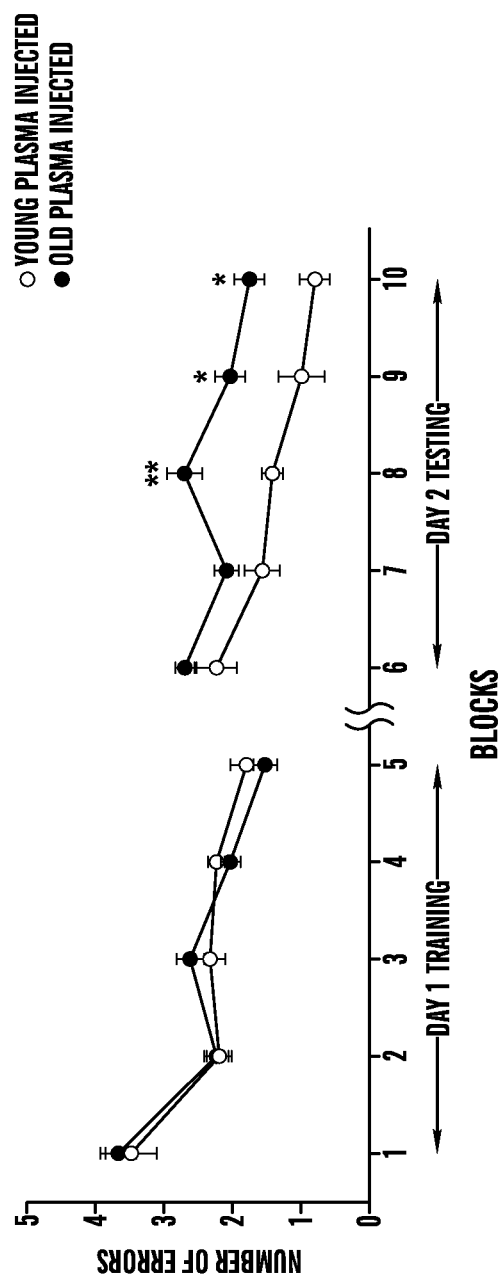

As previously reported by others (Ajami et al., Nat Neurosci (2007) 10: 1538-1543), we rarely detected peripherally derived GFP cells in the CNS of wild-type mice when joined to GFP transgenic mice, and these numbers did not differ between isochronic and heterochronic pairings (FIG. 8E), suggesting the observed effects are most likely mediated by soluble factors in plasma. To confirm that circulating factors within aged blood can contribute to reduced neurogenesis with age, we intravenously injected plasma isolated from young (3-4 months) and old (18-22 months) mice into a cohort of young adult animals. The number of Dcx-positive cells in the DG decreased in animals receiving old plasma compared to animals receiving young plasma (FIG. 2A), indicating that soluble factors present in old blood inhibit adult neurogenesis. To further investigate the functional effect of the aging systemic milieu on the young adult brain, extracellular electrophysiological recordings were done on hippocampal slices prepared from young isochronic and heterochronic parabionts (FIG. 2B). We detected a decrease in LTP levels in the medial and lateral DG of heterochronic parabionts compared to isochronic parabionts (FIG. 2C), indicating that age-related systemic changes can elicit deficits in synaptic plasticity. Lastly, given that LTP is considered a correlate of learning and memory (Bliss & Collingridge, Nature (1993) 361: 31-39), we sought to further evaluate the physiological effect of circulating factors present in aged blood by testing hippocampal dependent learning and memory using the RAWM paradigm in young adult mice intravenously injected with young or old plasma (FIG. 2D-2E). All mice showed similar spatial learning capacity during the training phase (FIG. 2E). However, during the testing phase animals administered with old plasma demonstrated impaired learning and memory for platform location, committing more errors in identifying the target arm compared to animals receiving young plasma (FIG. 2E). Collectively, these data indicate that factors present in aging blood inhibit adult neurogenesis, and moreover functionally contribute to impairments in synaptic plasticity and cognitive function.

Figure 3A:
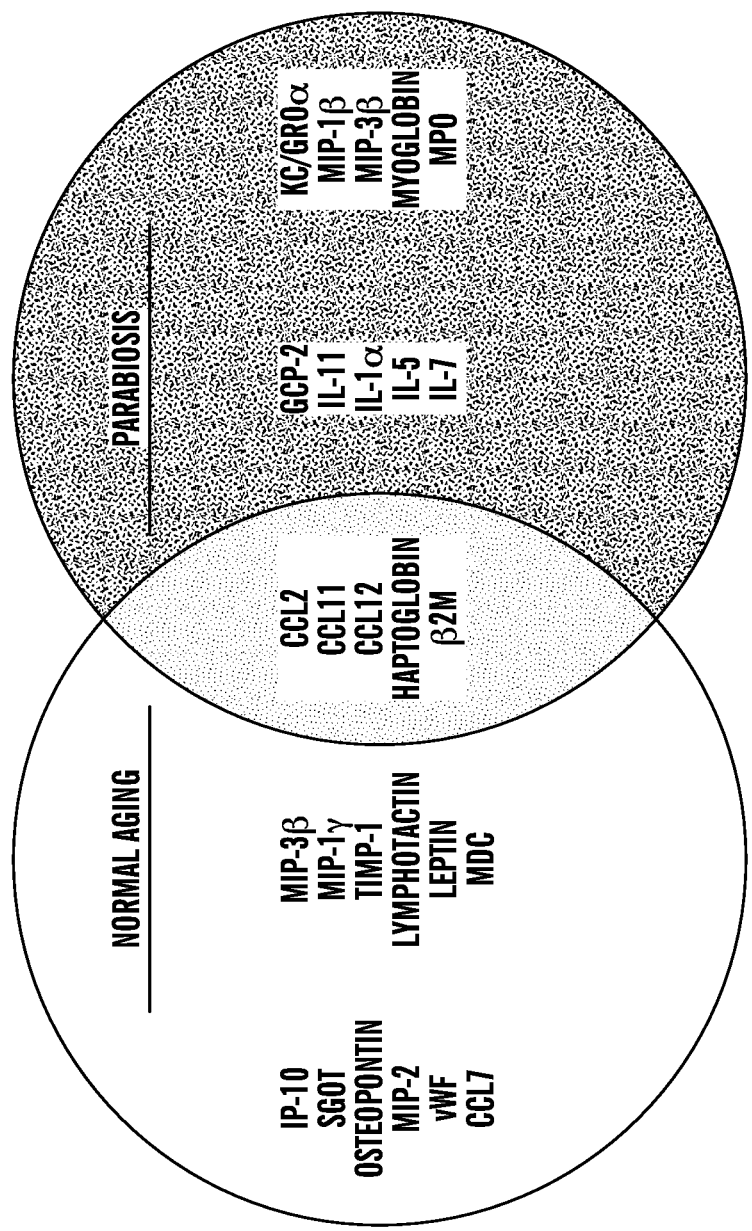
Figure 3F:
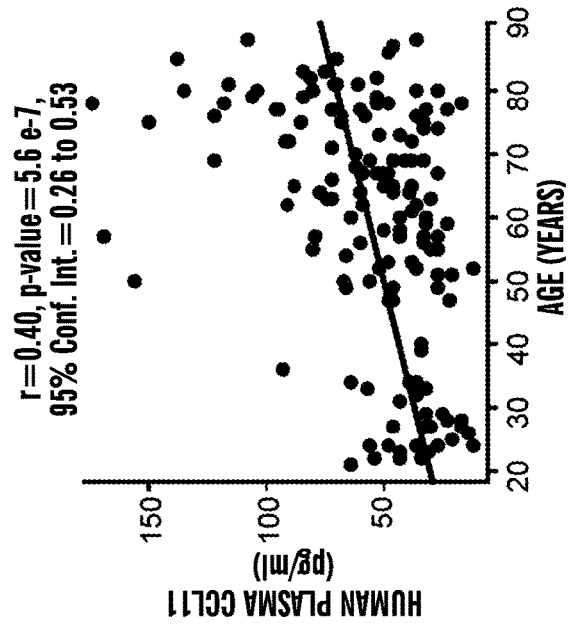
Figure 3G:
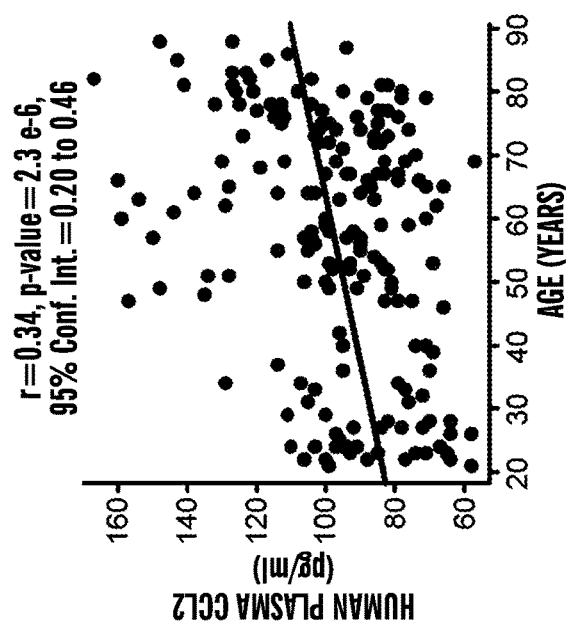
Figure 9B:
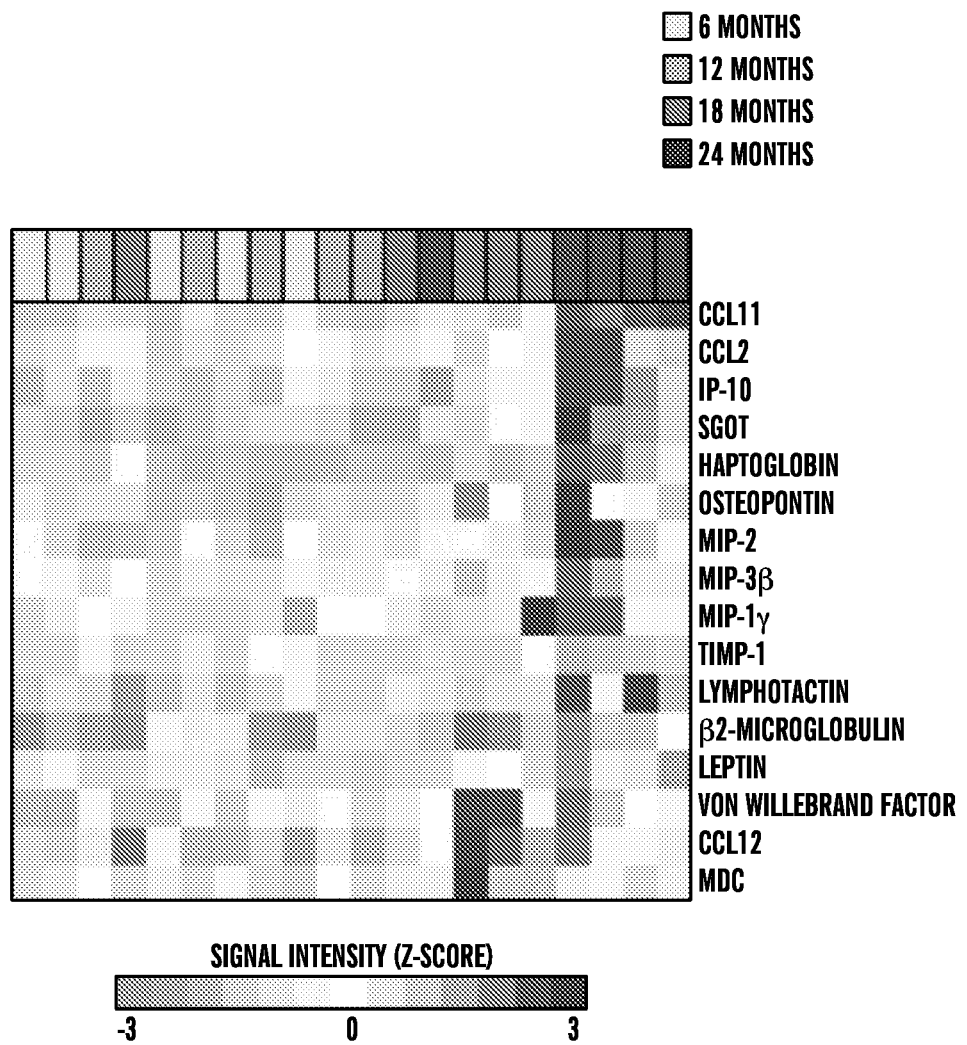

Consistent with our cellular findings in the CNS, previous studies focusing on muscle stem cells also show that exposure of the aged stem cell niche to a young systemic environment through heterochronic parabiosis results in increased regeneration after muscle injury (Conboy et al., Nature (2005) 433 760-764). However, in these earlier models individual circulating factors associated with either aging and tissue degeneration, or tissue rejuvenation, have remained elusive. To identify such systemic factors, we employed a proteomic approach in which the relative levels of 66 cytokines, chemokines and other secreted signaling proteins were measured in the plasma of normal aging mice using standardized antibody-based immunoassays on microbeads. Using multivariate analysis, we identified seventeen blood borne proteins that correlated with the age-related decline in neurogenesis during normal aging (FIG. 3A, 9A-9B).

To identify systemic factors associated with heterochronic parabiosis, we analyzed plasma samples from young and old animals before and after pairings in an independent proteomic screen using the Luminex platform. Comparison of young isochronic and heterochronic cohorts identified fourteen factors with a greater than 2-fold increase in expression in the heterochronic parabionts (FIG. 3A, FIG. 9C), while comparison between old isochronic and heterochronic cohorts revealed four factors whose expression levels decreased to less than 70% of that observed in isochronic parabionts (FIG. 9C). Interestingly, only five factors—CCL2, CCL11, CCL12, β2-microglobulin and Haptoglobin—were elevated in both old unpaired and young heterochronic cohorts compared to young unpaired or isochronic cohorts (FIG. 3A). We observed a comparable increase in the relative levels of CCL2 and CCL11 in the plasma of mice during normal aging (FIG. 3B-3C) and within young mice during heterochronic parabiosis (FIG. 3D-3E).

Figure 3H:
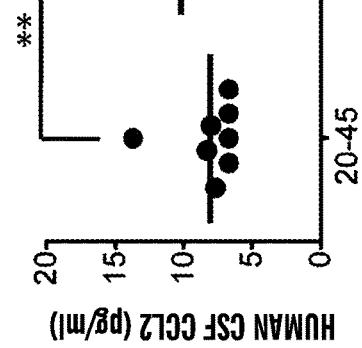
Figure 3I:
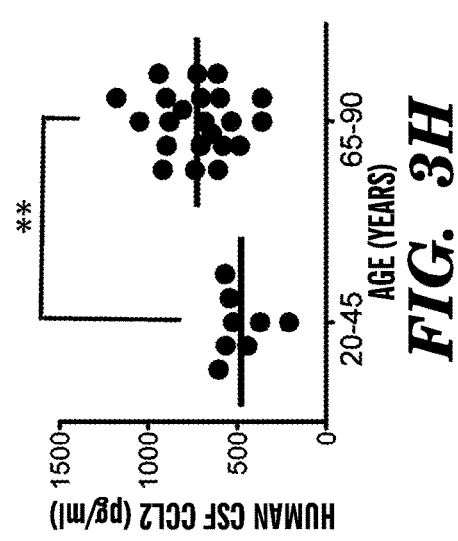

To corroborate systemic changes in mice with changes occurring in humans, we measured CCL2 and CCL11 in archived plasma and cerebrospinal fluid (CSF) samples from healthy individuals between 20 and 90 years of age. Indeed, we detected an age-related increase in CCL2 and CCL11 measured in both plasma (3F-3G) and CSF (FIG. 3H-3I), suggesting that these age-related systemic molecular changes are conserved across species.

Figure 4B:
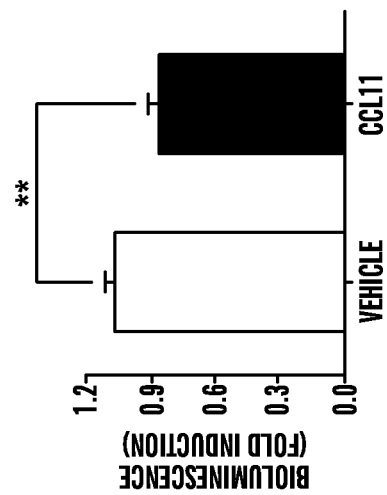
FIGS. 4A-4G show that systemic exposure to the age-related chemokine CCL11 inhibits neurogenesis and impairs spatial learning and memory in young adult animals.
Figure 4A:
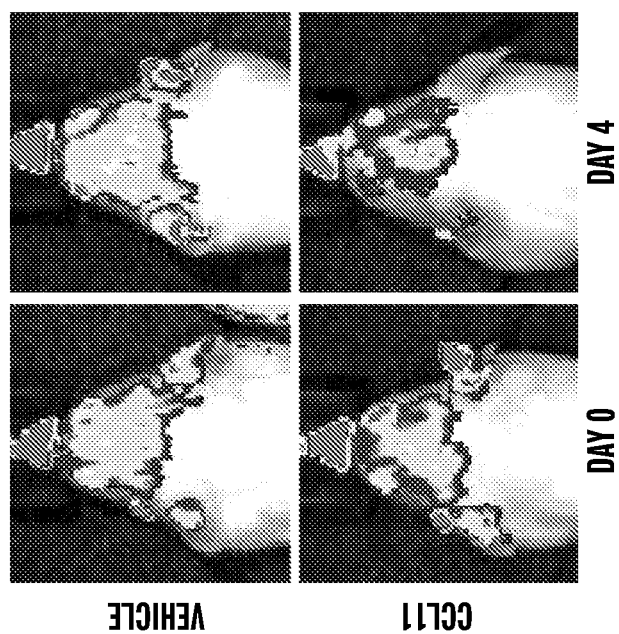

Having identified systemic factors associated with aging and decreased neurogenesis, we tested their potential biological relevance in vivo. As CCL2 had previously been linked to aging (Fumagalli & d'Adda di Fagagna, Nat Cell Biot (2009) 11: 921-923) and shown to regulate NPC function after brain injury (Belmadani et al., J Neurosci (2006) 26: 3182-3191), we decided to focus our study on CCL11, a chemokine involved in allergic responses and not previously linked to aging, neurogenesis, or cognition. We administered recombinant murine CCL11 protein through intraperitoneal injections into young adult mice and measured global changes in neurogenesis within the same mouse with a non-invasive bioluminescent imaging assay using Doublecortin-luciferase reporter mice (Couillard-Despres et al., Mol Imaging (2008) 7: 28-34). This systemic administration of recombinant CCL11 caused a significant decrease in Dcx promoter-dependent luciferase activity compared with mice receiving vehicle control indicating a decrease in the number of Dcx-expressing neuroblasts (FIG. 4A-4B).

Figure 4E:
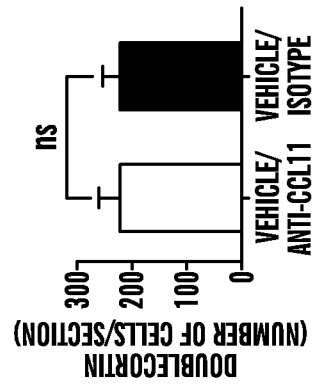
Figure 4F:
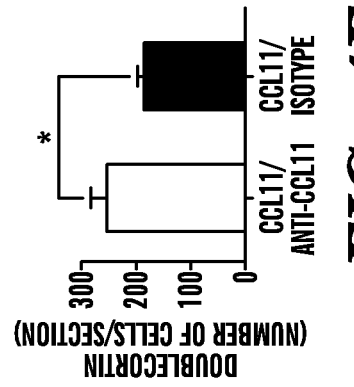
Figure 4C:
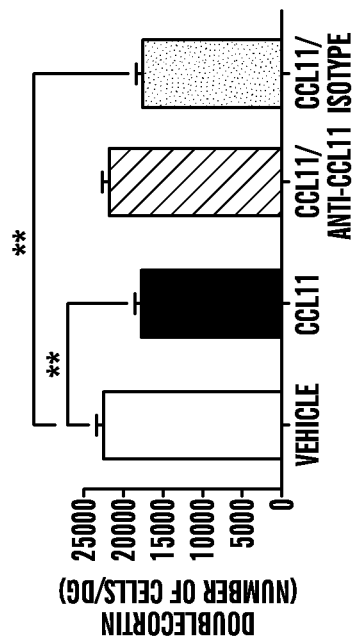
Figure 4D:
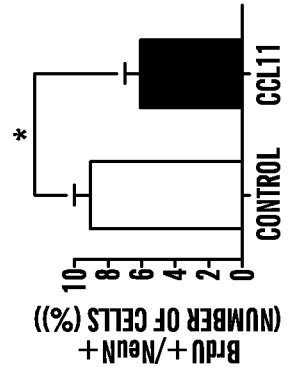
Figure 10A:
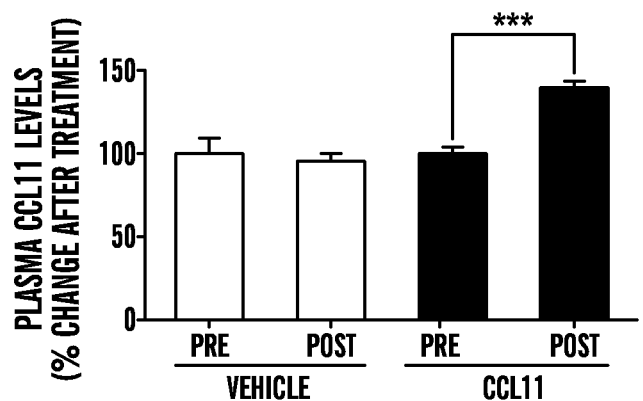
FIGS. 10A-C show that systemic administration of CCL11 reduces cell proliferation but not glial differentiation in the DG of young animals. Young adult male mice (2-3 months old) were injected with either recombinant murine CCL11 or PBS (vehicle) through intraperitoneal injections every three days for ten days for a total of four injections Animals were injected with BrdU for three days prior to sacrifice.
Figure 10B:
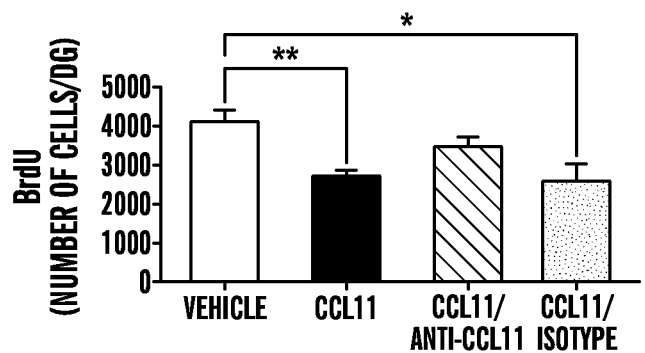
Figure 10C:
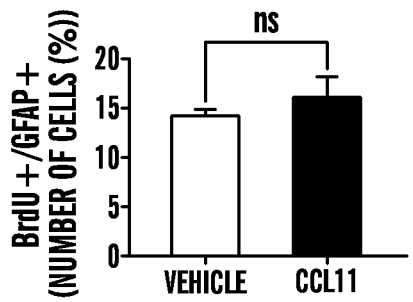
Figure 11A:
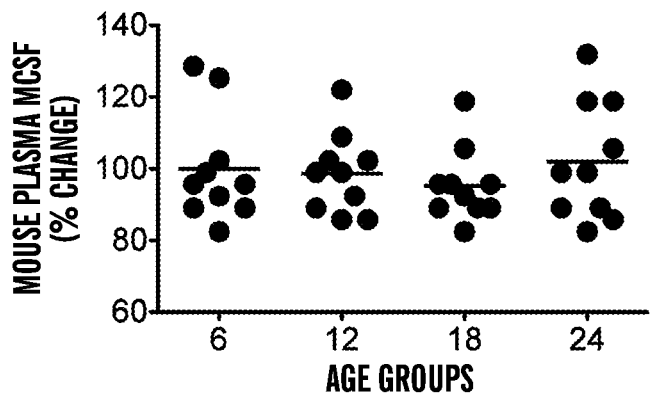
Figure 11B:
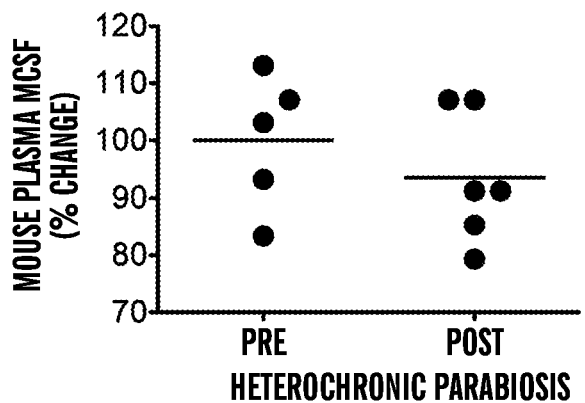
Figure 11C:
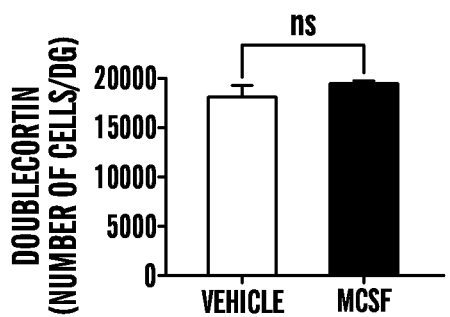
FIG. 11C shows quantification of neurogenesis in the DG after systemic drug administration. Data are from 5 mice per group (5 sections per mouse). Bars show mean±SEM; n.s, not significant; t-test (11B and 11C) or ANOVA, Dunnet's post-hoc test (11A).

To confirm and expand upon this in vivo bioluminescent model, we next investigated the effect of systemic CCL11 on adult hippocampal neurogenesis using immunohistochemical analysis. In an independent cohort of young wild type adult mice, we administered recombinant CCL11 or vehicle alone, and in combination with either an anti-CCL11 neutralizing antibody or an isotype control antibody through intraperitoneal injections. The systemic administration of recombinant CCL11 induced an increase in CCL11 plasma levels (FIG. 10A), and caused a significant decrease in the number of Dcx-positive cells in the DG compared to mice injected with vehicle control, consistent with in vivo bioluminescent results (FIG. 4C). Importantly, this decrease in neurogenesis could be rescued by systemic neutralization of CCL11 (FIG. 4C). Likewise, BrdU-positive cells also showed similar changes in cell number (FIG. 10C), and furthermore the percentage of cells expressing both BrdU and NeuN decreased after systemic administration of CCL11 (FIG. 4D). The percentage of cells expressing BrdU and GFAP did not significantly change (FIG. 10C). As a negative control we assayed neurogenesis in a cohort of young adult mice after systemic administration of monocyte colony stimulating factor (MCSF), a protein measured in both of our independent proteomic screens that did not show an age-dependent change in plasma levels or a correlation with reduced neurogenesis, and detected no change in Dcx-positive cells in the DG (FIG. 11A-11C). Together, these data indicate that increasing the systemic level of CCL11, an individual age-related factor identified in our unbiased screen, is sufficient to partially recapitulate some of the inhibitory effects on neurogenesis observed with aging and heterochronic parabiosis.

Figure 12A:
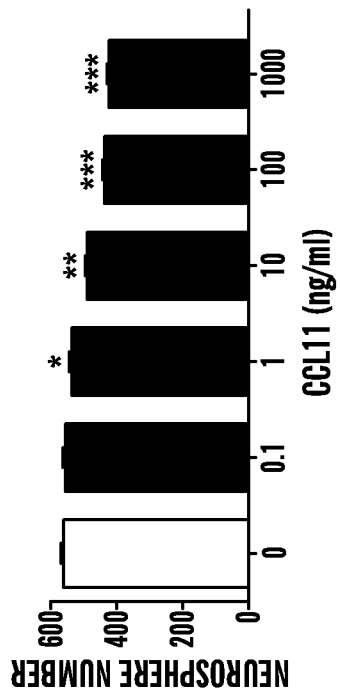
Figure 12B:
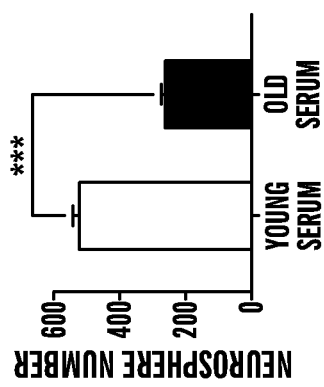
Figure 12C:
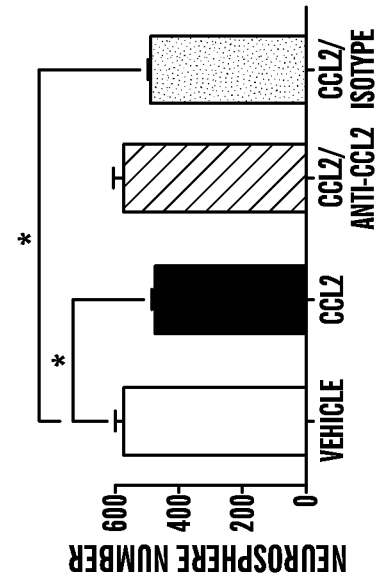
Figure 12D:
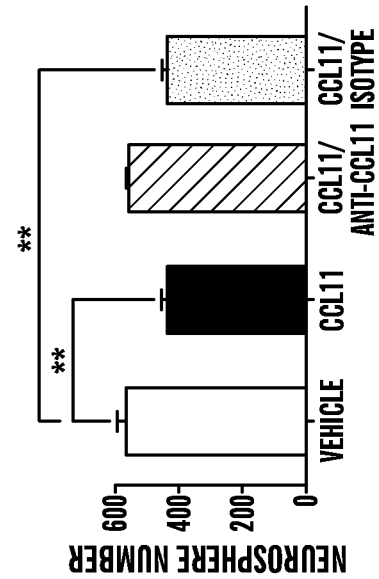

To investigate the possibility that age-related blood borne factors can directly influence stem cell function, we used primary mouse NPC cultures as a model of neural stem cell activity. We observed a 50% decrease in the number of neurospheres formed after a four-day exposure of NPCs to aged mouse serum when compared to NPCs exposed to young serum (FIG. 12A). We then tested whether the identified chemokines could also exert an inhibitory effect on NPCs and neural differentiation in vitro. The number of neurospheres formed from primary NPCs significantly decreased in the presence of either recombinant CCL11 (FIG. 12B-12C) or CCL2 (FIG. 12D). Additionally, neurosphere size also decreased in the presence of CCL11 (FIG. 12E-12F). Using a human derived NTERA cell line expressing eGFP under the Doublecortin promoter, we assayed neural differentiation and observed a significant decrease in eGFP expression after twelve days in culture with either CCL11 (FIG. 12G) or CCL2 (FIG. 12H) under differentiation conditions. Our data demonstrate that inhibitory factors present in aged blood are sufficient to act directly on NPCs in vitro. While these findings, together with studies showing a lack of a classical BBB in the neurogenic niche 13-15, open the possibility of a direct interaction of systemic factors with progenitor cells in vivo during aging, they do not preclude the possibility that age-related systemic factors may also act indirectly by stimulating other cell types that comprise the neurogenic niche to release additional inhibitory factors.

Figure 13:
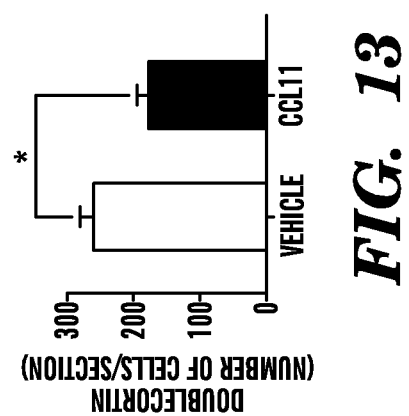
FIG. 13 shows that neurogenesis is inhibited by direct exposure to CCL11 in vivo. Young adult mice were injected stereotaxically with either recombinant CCL11 or PBS into the left or right DG. Dcx-positive cells in adjacent sides of the DG within the same section were shown for treatment groups. Quantification of neurogenesis in the DG after stereotactic CCL11 administration is shown. All data are from 4-5 young adult mice (2-3 months of age) per group (5 sections per mouse). Bars show mean±SEM; *, P<0.05, t-test

To examine the direct effect of CCL11 on neurogenesis in the brain, we stereotaxically injected recombinant CCL11 into the DG of young adult mice, and observed a decrease in the number of Dcx-positive cells when compared with the contralateral DG receiving vehicle control (FIG. 13). Furthermore, as an additional test of direct actions of systemic factors in the brain, we examined whether the inhibitory effect of peripheral CCL11 on neurogenesis could be restored locally by inhibiting CCL11 action specifically within the hippocampus. To test this, we stereotaxically injected CCL11-specific neutralizing antibody into the DG and isotype control antibodies into the contralateral DG of young adult mice. Following stereotaxic injection, we systemically administered either recombinant CCL11 or vehicle control by intraperitoneal injections. The decrease in Dcx-positive cell number observed in animals receiving systemic CCL11 administration could be rescued by neutralizing CCL11 within the DG with antigen specific antibodies but not isotype controls (FIG. 4E-4F), suggesting that increases in systemic chemokine levels exert a direct effect in the CNS.

Figure 4G:
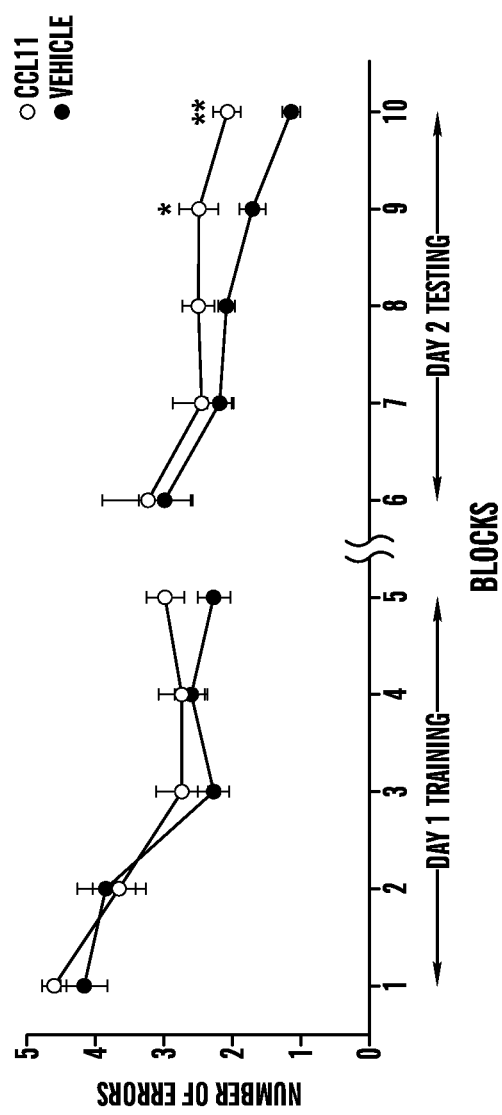
Figure 5A:
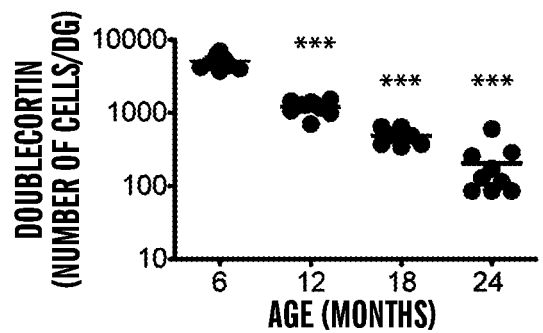
FIGS. 5A-5D show that adult neurogenesis decreases as neuroinflammation increases in the DG during aging. We performed an immunohistochemical detection of newly differentiated Doublecortin (Dcx)-positive neurons, long-term BrdU-retaining cells (arrowheads), CD68-positive activated microglia, and GFAP-positive astrocytes in the DG of the hippocampus from adult mice at 6 and 18 months of age.
Figure 5C:
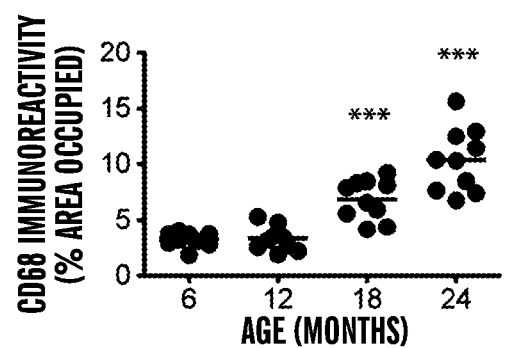
Figure 5B:
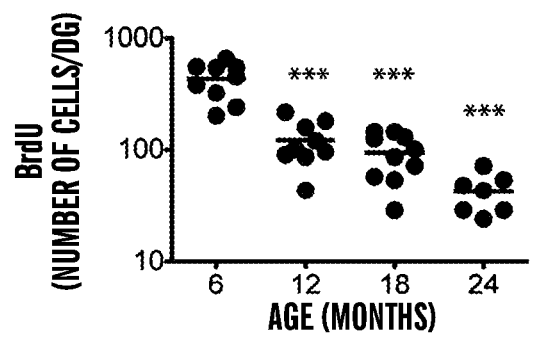
Figure 5D:
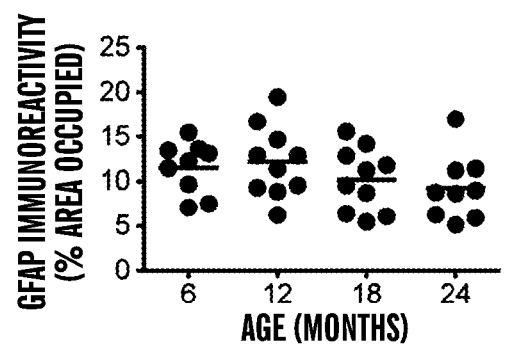

Finally, to determine the physiological relevance of increased systemic CCL11 levels in mice we assessed hippocampal dependent learning and memory using the RAWM paradigm (FIG. 2D). Cohorts of young adult mice received intraperitoneal injections of recombinant murine CCL11 or PBS vehicle as a control. All mice showed similar spatial learning capacity during the training phase regardless of treatment (FIG. 4G). However, by the end of the testing phase animals receiving recombinant CCL11 protein exhibited impaired learning and memory deficits, committing significantly more errors in locating the target platform than animals receiving vehicle control (FIG. 4G). Together, these functional data demonstrate that increasing the systemic level of CCL11 not only inhibit adult neurogenesis but also impair hippocampal dependent learning and memory.

Figure 14A:
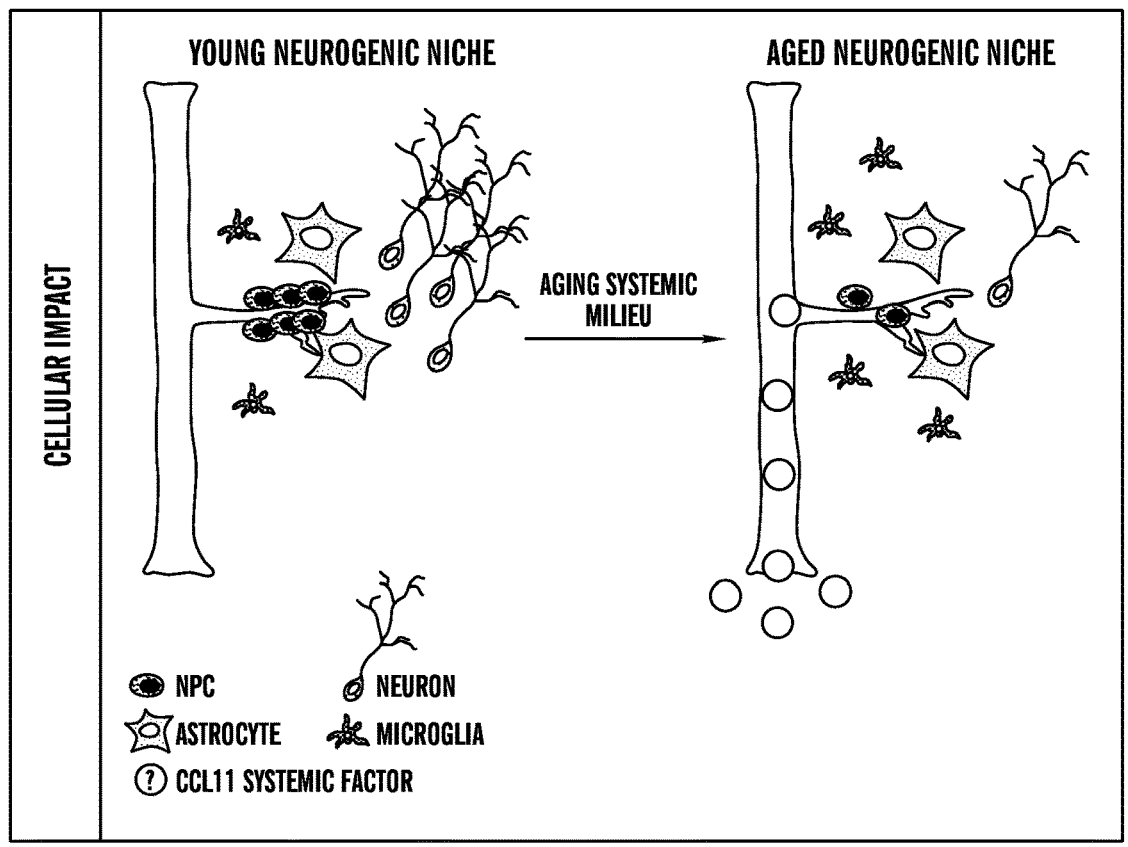
FIGS. 14A-14B show a proposed model illustrating the cellular and functional impact of age-related systemic molecular changes on the adult neurogenic niche. Schematic of cellular changes occurring in the neurogenic niche during normal aging and heterochronic parabiosis. Levels of blood-borne factors, including the chemokines CCL11 and CCL2, increase during normal aging and heterochronic parabiosis. These systemic changes contribute to the decline in neurogenesis observed in the adult brain and functionally impair synaptic plasticity and learning and memory. Cellular impact illustration is provided in FIG. 14A and functional impact scenario is provided in FIG. 14B. Cell types illustrated include neural stem cells (NPC), neurons, astrocytes, and microglia (FIG. 14A).
Figure 14B:
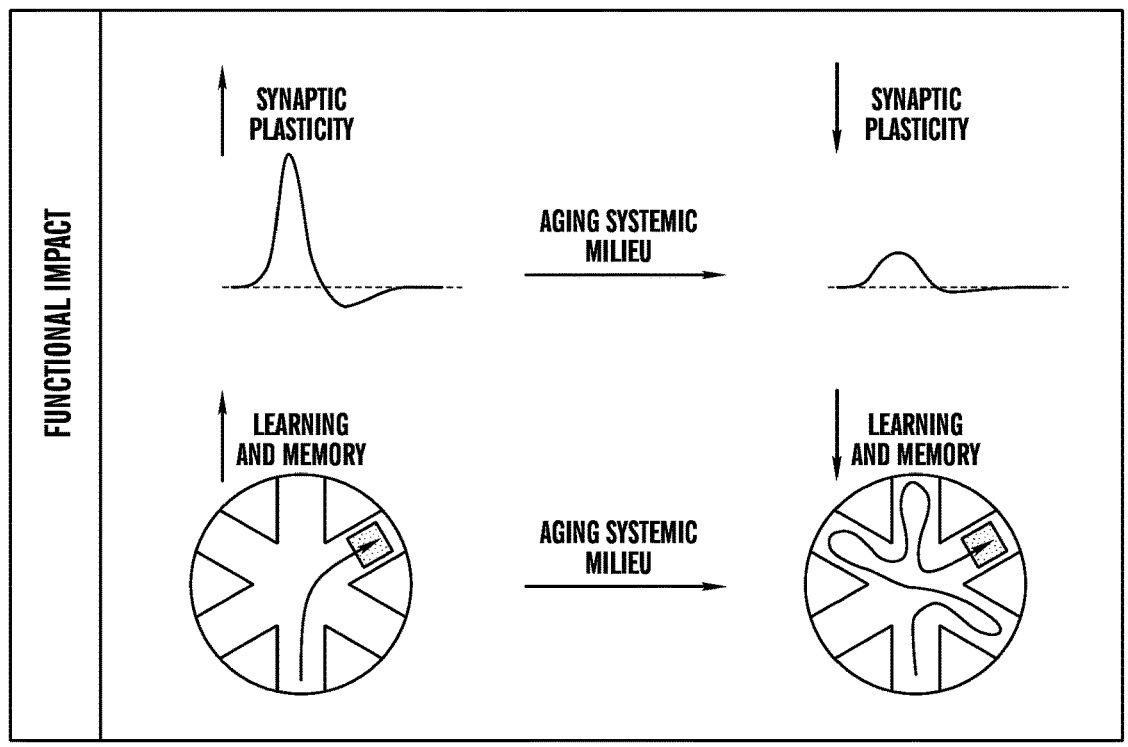

Cumulatively, our data link age-related molecular changes in the systemic milieu to the age-related decline in adult neurogenesis and associated impairments in synaptic plasticity and cognitive function observed during aging (FIGS. 14A-14B). We demonstrate that the influence of the aging systemic milieu is significant, and one that changes in an age-dependent fashion, potentially contributing to the susceptibility of the aging brain to cognitive impairments. The proteomic platform we used here was suitable to identify age-related systemic factors which inhibit adult neurogenesis.

We now show that an increase in the systemic levels of immune-related factors present in old blood is capable of diminishing adult neurogenesis and impairing spatial learning and memory. We identified age-related chemokines classically involved in peripheral inflammatory responses as biologically relevant inhibitory factors of neurogenesis in cell culture and in the CNS. Interestingly, CCL2, CCL11 and CCL12 are localized to within 70 kB on mouse chromosome 11, and likewise, CCL2 and CCL11 are within 40 kB on human chromosome 17 (mouse CCL12 is a homologue of human CCL2 and does not exist in humans), implicating this genetic locus in normal brain aging and possibly aging in general. Indeed, work investigating cellular senescence, a known hallmark of aging, furthers the involvement of some of the individual systemic chemokines reported here (CCL2) in the aging process as components of the Senescence-Associated Secretory Phenotype (Fumagalli, M. & d'Adda di Fagagna, F., Nat Cell Biol 11 (8), 921-923 (2009)).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating an adult mammal for a cognitive symptom of an aging-associated impairment, the method comprising:
    modulating C-C chemokine receptor type 3 (CCR3) in the mammal in a manner sufficient to treat the adult mammal for the cognitive symptom of the aging-associated impairment.

2. The method according to claim 1, wherein modulating CCR3 comprises modulating eotaxin-1/CCR3 interaction.

3. The method according to claim 2, wherein eotaxin-1/CCR3 interaction is modulated by reducing active systemic eotaxin-1 in the mammal.

4. The method according to claim 3, wherein the active systemic eotaxin-1 is reduced in the mammal by administering to the mammal an effective amount of an active systemic eotaxin-1 reducing agent.

5. The method according to claim 4, wherein the active systemic eotaxin-1 reducing agent is an eotaxin-1 binding agent.

6. The method according to claim 5, wherein the eotaxin-1 binding agent comprises an antibody or binding fragment thereof.

7. The method according to claim 5, wherein the eotaxin-1 binding agent comprises a small molecule.

8. The method according to claim 4, wherein the active systemic eotaxin-1 reducing agent comprises an eotaxin-1 expression inhibitory agent.

9. The method according to claim 8, wherein the eotaxin-1 expression inhibitory agent comprises a nucleic acid.

10. The method according to claim 1, wherein eotaxin-1/CCR3 interaction is modulated by reducing CCR3 activity in the mammal.

11. The method according to claim 10, wherein the CCR3 activity is reduced in the mammal by administering to the mammal an effective amount of an active CCR3 reducing agent.

12. The method according to claim 11, wherein the active CCR3 reducing agent is a CCR3 binding agent.

13. The method according to claim 12, wherein the CCR3 binding agent comprises an antibody or binding fragment thereof.

14. The method according to claim 12, wherein the CCR3 binding agent comprises a small molecule.

15. The method according to claim 11, wherein the active CCR3 reducing agent comprises a CCR3 expression inhibitory agent.

16. The method according to claim 15, wherein the CCR3 expression inhibitory agent comprises a nucleic acid.

17. The method according to claim 1, wherein the mammal is a primate.

18. The method according to claim 17, wherein the primate is a human.

19. The method according to claim 1, wherein the elderly mammal is a human that is 60 years or older.

20. The method according to claim 1, wherein the aging-associated impairment comprises a cognitive impairment.

21. The method of claim 1, wherein treating the cognitive symptom of the aging-associated impairment comprises increasing neurogenesis.

22. The method of claim 1, wherein treating the cognitive symptom of the aging-associated impairment comprises increasing synaptic plasticity.

23. The method of claim 1, wherein the cognitive symptom comprises impaired learning.

24. The method of claim 1, wherein the cognitive symptom comprises impaired memory.

* * * * *